United States Patent [19]
Gilmartin

[11] Patent Number: 5,795,453
[45] Date of Patent: Aug. 18, 1998

[54] ELECTRODES AND METALLO ISOINDOLE RINGED COMPOUNDS

[76] Inventor: Markas A. T. Gilmartin, 18 Westbrook Court, Cumberland Close, Baltic Wharf, Bristol BS16XB, England

[21] Appl. No.: 589,912

[22] Filed: Jan. 23, 1996

[51] Int. Cl.$^6$ ............... G01N 27/26; G01N 33/50; C12Q 1/00
[52] U.S. Cl. ............. 204/403; 205/777.5; 205/778; 435/817
[58] Field of Search ............. 204/403; 205/777.5, 205/792, 778; 435/817

[56] References Cited

U.S. PATENT DOCUMENTS

| | | | |
|---|---|---|---|
| 3,753,782 | 8/1973 | Beccu et al. | 429/221 |
| 3,860,642 | 1/1975 | Rutledge | 562/531 |
| 4,172,022 | 10/1979 | Lidorenko et al. | 204/426 |
| 4,193,983 | 3/1980 | Ullman et al. | 436/528 |
| 4,405,693 | 9/1983 | Doddapaneni | 429/101 |
| 4,487,669 | 12/1984 | Kuwana | 570/252 |
| 4,541,908 | 9/1985 | Niki et al. | 205/334 |
| 4,560,534 | 12/1985 | Kung et al. | 422/68 |
| 4,613,551 | 9/1986 | Doddapaneni | 429/194 |
| 4,711,245 | 12/1987 | Higgins et al. | 128/635 |
| 4,830,959 | 5/1989 | McNeil et al. | 435/7 |
| 4,836,904 | 6/1989 | Armstrong et al. | 204/294 |
| 4,840,893 | 6/1989 | Hill et al. | 435/6 |
| 4,871,442 | 10/1989 | Yamaguchi et al. | 204/403 |
| 4,897,173 | 1/1990 | Nankai et al. | 204/403 |
| 4,921,586 | 5/1990 | Molter | 205/338 |
| 4,923,586 | 5/1990 | Katayama et al. | 204/403 |
| 4,927,516 | 5/1990 | Yamaguchi et al. | 204/403 |
| 4,933,052 | 6/1990 | O'Brien et al. | 205/108 |
| 4,957,615 | 9/1990 | Ushizawa et al. | 204/415 |
| 5,078,856 | 1/1992 | Yamaguchi et al. | 204/418 |

(List continued on next page.)

FOREIGN PATENT DOCUMENTS

| | | |
|---|---|---|
| 0 127 958 A2 | 8/1984 | European Pat. Off. |
| 0 127 958 B1 | 8/1984 | European Pat. Off. |
| 0 251 915A | 1/1988 | European Pat. Off. |
| PCT/US93/00624 | 1/1993 | WIPO |
| PCT/US93/00626 | 1/1993 | WIPO |

OTHER PUBLICATIONS

Patent Abstracts of Japan, vol. 16, No. 407:1411, Aug. 27, 1992, JP 04 136749A (Terumo Corp.), May 11, 1992.

Taraszewska, J. et al., "Electrochemical behavior of nickel tetraazamacrocyclic complexes incorporated into carbon paste electrodes: application in $H_2O_2$ electrocatalysis," Journal of Electroanalytical Chemistry, vol. 371:223–230 (1994), XP000671097. Month available.

Wring et al. ("Chemically modified, screen–printed carbon electrodes", Analyst (London) (1992), 117(8), 1281–6), month unknown.

Gilmartin et al. ("Development of One–shot Biosensors for the MEasurement of Uric Acid and cholesterol", Analytical Proceedings Including Analytical Communications, Aug. 1995, vol. 32, pp. 341–345).

Christie et al. (CAPLUS abstract of "Plasticized poly (vinyl chloride) as a permselective barrier membrane for high–selectivity amperometric sensors and biosensors", Anal. Chim. Acta (1992), 269(1), 65–73), month unknown.

Geise et al. (CAPLUS abstract of "Electropolymerized films to prevent interferences and electrode fouling in biosensors", Biosens. Bioelectron. (1991), 6(2), 151–60), month unknown.

(List continued on next page.)

*Primary Examiner*—Kathryn L. Gorgos
*Assistant Examiner*—Alex Noguerola
*Attorney, Agent, or Firm*—Cooley Godward LLP

[57] ABSTRACT

The present invention provides for electrode assemblies and methods in which electron transfer between a redox reaction product and an electrically conductive electrode material is facilitated by a metallo macrocyclic compound, preferably a metallo isoindole ringed compound and more preferably a ferro isoindole ringed compound. The redox reaction is usually catalysized by a redox enzyme, such as an oxidase.

21 Claims, 5 Drawing Sheets

U.S. PATENT DOCUMENTS

| | | | |
|---|---|---|---|
| 5,135,717 | 8/1992 | Renzoni et al. | 422/61 |
| 5,205,920 | 4/1993 | Oyama et al. | 204/403 |
| 5,332,662 | 7/1994 | Ullman | 435/28 |
| 5,346,670 | 9/1994 | Renzoni et al. | 422/52 |
| 5,356,786 | 10/1994 | Heller et al. | 204/403 |
| 5,378,628 | 1/1995 | Grätzel et al. | 204/403 |
| 5,411,647 | 5/1995 | Johnson et al. | 205/777.5 |
| 5,413,690 | 5/1995 | Kost et al. | 204/403 |
| 5,419,854 | 5/1995 | Wakabayashi et al. | 252/583 |
| 5,509,410 | 4/1996 | Hill et al. | 128/637 |

OTHER PUBLICATIONS

Batchelor et al. ("Amperometric assay for the ketone body 3-hydroxybutyrate", Analytica Chimica Acta, 221(1989) 289–294), month unknown.

WPIDS abstract of JP08304327 (Oji Paper Co), Nov. 22, 1996.

Budavari, ed., The Merck Index: An Encyclopedia of Chemicals, Drugs and Biologicals month unavailable.

Cai, et al., Indium–Tin Oxide Film Electrode as Catalytic Amperometric Sensor for Hydrogen Peroxide, Analyst, 120:2579–2582 (Oct. 1995).

Cox, et al., Voltammetric Reduction and Determination of Hydrogen Peroxide at an Electrode Modified with a Film Containing Palladium and Iridium, Anal. Chem. 61:2176–2178 (1989) month unavailable.

Gamburzev, et al., Enzyme Electrodes with Pyrolyzed CoT-MPP Catalyst, Electroanalysis, 3:865–867 (1991) month unavailable.

Gilmartin, et al., Fabrication and Characterization of a Screen–printed, Disposable, Amperometric Cholesterol Biosensor, Analyst, 119:2331:2336 (Nov. 1994).

Gilmartin, et al., Rapid Detection of Paracetamol Using a Disposable, Surface–modified Screen–printed Carbon Electrode, Analyst, 119:2431–2437 (Nov. 1994).

Gilmartin, et al., Sensing With Chemically and Biologically Modified Carbon Electrodes: A Review, Analyst, 120:1029–1045 (Apr. 1995).

Gilmartin, et al. Novel, Reagentless, Amperometric Biosensor for Uric Acid Based on a Chemically Modified Screen–printed Carbon Electrode Coated with Cellulose Acetate and Uricase, Analyst, 119:833–840 (May 1994).

Gilmartin, et al., Development of One–shot Biosensors for the Measurement of Uric Acid and Cholesterol, Analytical Proceedings Including Analytical Communications, 32:341–345 (Aug. 1995).

Gilmartin, et al., Enzymes and Electrodes—A Marriage of Convenience, Biologist 42:213–216 (1995) month unavailable.

Grant, et al., Grant & Hackh's Chemical Dictionary, p. 448 (1987) month unavailable.

Linders, et al., Catalase Like Activity of Iron Phthalocyanine Incorporated in a Carbon Paste Electrode, Analytical Letters 19:1831–1837 (1986) month unavailable.

Mannino, et al., Cobalt (II, III)–Oxide Chemically Modified Electrode as Amperometric Detector in Flow Injection Systems, Electroanalysis 5:145–148 (1993) month unavailable.

Oyama, et al., A Redox–Active Polymer Film Mediated Enzyme Electrode for Amperometric Determination of Free Cholesterol, Electroanalysis 3:665–671 (1991) month unknown.

Oyama, et al., Electropolymerized Cobalt Tetrakis (o–aminophenyl)porphyrin Film Mediated Enzyme Electrode for Amperometric Determination of Glucose, Anal. Chem. 60:2534–2536 (1988) month unknown.

Shiraishi, et al., Anodic Stripping Voltammetry of Uric Acid at Glassy Carbon Electrodes after Pre–Electrolysis in Solution Containing Copper (II), Analytical Sciences 10:133–135 (Feb. 1994).

Taha, et al., Electrocatalysis and Flow Detection at a Glassy Carbon Electrode Modified witha Thin Film of Oxymanganese Species, Electroanalysis 3215–3219 (1991) month unknown.

Tatsuma, et al., Enzyme Monolayer–and Bilayer–Modified Tin Oxide Electrodes for the Determination of Hydrogen Peroxide and Glucose, Anal. Chem. 61:2352–2355 (1989) month unknown.

Wring, et al., Voltammetric Behaviour of Screen–printed Carbon Electrodes, Chemically Modified With Selected Mediators, and Their Application as Sensors for the Determination of Reduced Glutathione, Analyst 116:123–129 (1991) month unknown.

ELECTRODES AND METALLO ISOINDOLE RINGED COMPOUNDS

TECHNICAL FIELD

The present invention relates electrodes with metallo ringed compounds and methods of using the same. Such electrodes are particularly useful in electrochemical assays of analytes using printed versions of the electrodes with oxidases.

BACKGROUND

The rapid development of the medical and life sciences continues to create an increasing demand for the rapid, accurate and sensitive detection of analytes. Rapid and convenient detection of analytes is imperative in a myriad of situations, such as emergency rooms (e.g., for acetaminophen, aspirin or alcohol detection in overdose cases), law enforcement situations (e.g. for illicit drug detection) and food factories (e.g., to detect microorganisms, waste products or toxins in spoiled or inferior quality produce). Modern health care has also demanded more home or point-of-care determinations of analytes for real-time diagnosis, patient management, and cost containment. In the environmental fields, a typical assessment of a sample, for instance for a water quality sample, involves lengthy and involved separations, extractions and incubations, and in some cases may take a day or more to complete. Such delays often lead to inaccurate results or the detrimental spread of pollution. Thus, new and efficient methods for performing a host of biochemical tests would be a welcome arrival in diagnostic-oriented fields.

Previously, hydrogen peroxide has been used extensively as an indicator molecule in analytical determinations. One significant development has been the construction of amperometric hydrogen peroxide sensors. Although this approach can provide an attractive route to measuring hydrogen peroxide, being simpler, faster and less expensive compared to chromatographic, and spectrophotometric counterparts, there are significant drawbacks to contemporary hydrogen peroxide sensors. Amperometric sensors configured for hydrogen peroxide detection are fraught with problems due to the high potentials needed to drive reactions that permit detection of the electro-chemical breakdown of hydrogen peroxide. This is true of both oxidation and reduction modes for measuring hydrogen peroxide, unless sophisticated surface design strategies are adopted to create sensory interfaces with more predictable properties. These approaches complicate sensor fabrication, lengthen response times and often compromise both the reliability and storage characteristics of the devices. Thus, the search for a one-step method for the manufacture of chemically modified electrodes with adept hydrogen peroxide electro-chemistries has remained unsolved until the advent of the invention described herein.

SUMMARY OF THE INVENTION

Until the development of the present invention, detection of analytes using electrodes, particularly electrodes designed for detecting hydrogen peroxide in small samples, were beset with technical limitations such as interferents, electrode sensitivity, electrode selectivity, and high voltage requirements. The present invention provides for electrode assemblies and methods in which electron transfer between a redox reaction product and an electrically conductive electrode material is facilitated by a metallo macrocyclic compound, preferably a metallo isoindole ringed compound and more preferably a ferro isoindole ringed compound. The redox reaction is usually catalysized by a redox enzyme, such as an oxidase.

The electrode assemblies of the invention can be configured with a macrocyclic compound in a variety of ways to facilitate 1) electrical contact between an electrode's electrode material and the metallo macrocyclic compound and 2) electrical contact between the metallo macrocyclic compound and a redox enzyme, such as an oxidase, if so desired. As described herein different electrodes and electrode assemblies can be achieved by 1) dispersing an metallo macrocyclic compounds in electrode material, 2) applying an metallo macrocyclic compound to the surface of the electrode, 3) applying a layer over the electrode comprising a metallo macrocyclic compound or 4) a combination thereof. Such assemblies permit low voltage measurements of analytes which reduces noise, increases selectivity and increases the signal to noise ratio.

Another embodiment of the invention is an electrode assembly comprising 1) a first hydrogen peroxide electrode comprising a metallo isoindole ringed compound dispersed in an electrode material, and 2) an first enzyme layer comprising a first enzyme and in electrical contact with said first hydrogen peroxide electrode. Such an electrode provides for excellent hydrogen peroxide selectivity, especially for the detection of hydrogen peroxide at low voltages. Preferably, the metallo isoindole ringed compound coordinates Fe, Ru, Rh, or Mn.

Another embodiment of the invention provides for an electrode, particularly a hydrogen peroxide electrode, that comprises a) a ferro isoindole ringed compound, b) an electrode, and c) an oxidase enzyme. The metallo isoindole ringed compound is provided in a sufficient amount to permit electron transfer between the electrode material and the oxidase product, usually hydrogen peroxide, and allows for detection of an electrical current related to catalysis by the oxidase.

The invention affords detecting analytes using a number of different assay formats. Generally, the method for electrically detecting the presence of an analyte comprises: 1) measuring an electrical current from a redox electrode comprising an electrode material and a ferro isoindole ringed compound in fluid communication with a redox enzyme, particularly a oxidase. The redox enzyme catalyses a redox reaction that corresponds to the presence of an analyte and produces a product that either 1) directly chemically oxidizes or reduces said ferro isoindole ringed compound or 2) indirectly oxidizes or reduces said ferro isoindole ringed compound. Because the present invention is particularly well suited for manufacture using printing techniques the methods and devices of the invention offer reliable, simple and cost effective analyte determinations for a myriad of applications in the health care, environmental, food, agriculture and law enforcement fields.

BRIEF DESCRIPTION OF THE DRAWINGS

FIG. 6 illustrates amperometric interference test using SPCEs containing $C_{32}H_{18}N_8Fe(II)$. Arrows show responses to successive additions of hydrogen peroxide, and the interferents, L-ascorbic acid, uric acid and paracetamol all at $0.5 \times 10^{-3}$ mol dm$^{-3}$ final concentrations. Electrodes biased at −0.1 V (SCE) other conditions as in FIG. 5.

DESCRIPTION OF SPECIFIC EMBODIMENTS

INTRODUCTION

Until the development of the present invention, detection of analytes using electrodes, particularly electrodes designed for detecting hydrogen peroxide in small samples, were beset with technical limitations relating to interferents, electrode sensitivity, electrode selectivity, slow response times, mediator leaching, complicated electrode manufacture, high voltage requirements and noisy signals that thwarted signal transduction. The present invention provides for electrode assemblies and methods in which electron transfer between a redox reaction product and an electrically conductive electrode material is facilitated by a metallo macrocyclic compound, preferably a metallo isoindole ringed compound. The redox reaction is usually catalysized by an enzyme, such as an oxidase.

Metallo macrocyclic compounds, particularly ferro isoindole ringed compounds, on electrode surfaces can promote the catalytic reduction of hydrogen peroxide according to the following electro-chemical reaction pathway:

In effect, the natural biological catalysts, peroxidases, can be replaced in reaction (1) by a chemical analog of the enzyme's prosthetic heme group. Thus, bio-susceptibility to external factors is drastically minimized with an attendant enhancement in the electrode's observed stability patterns and performance. As these devices can be created simply, reproducibly and on a large-scale basis they provide an elegant means of generating single-use hydrogen peroxide cathodes.

Figure 1:
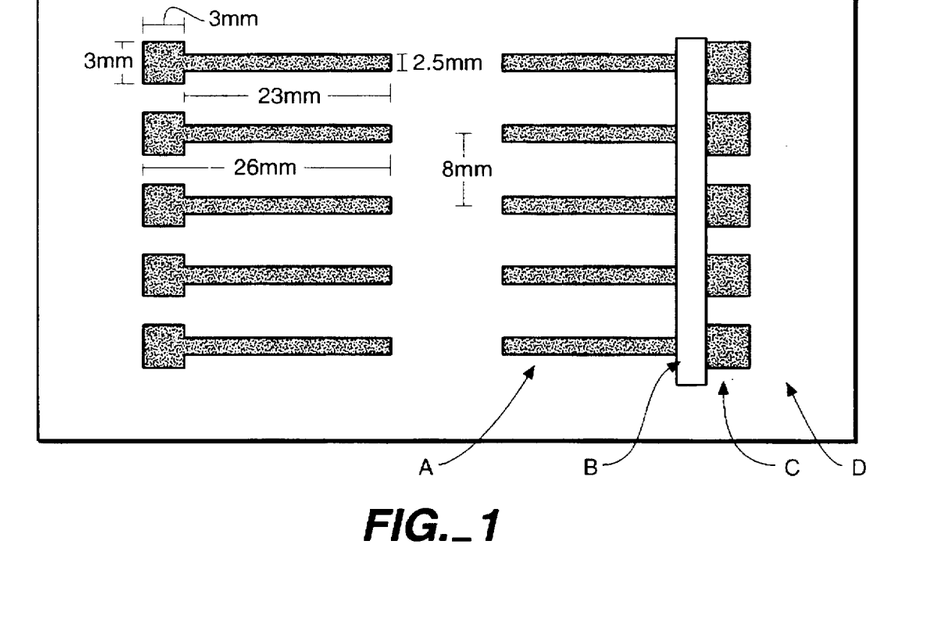
FIG. 1 illustrates a diagrammatic representation of a screen printed electrode assembly arrangement and geometry that can be used to measure multiple analytes simultaneously. Connecting strip A can be inserted into a spade connector to a potentiostat during operation. An insulation strip B can be provided for by means of a 3 mm wide strip of tape or preferably an insulating layer. The working area C can be used as a detection zone. D depicts an inert solid support, such as PVC (polyvinyl chloride), for a screen printed electrode.
Figure 2:
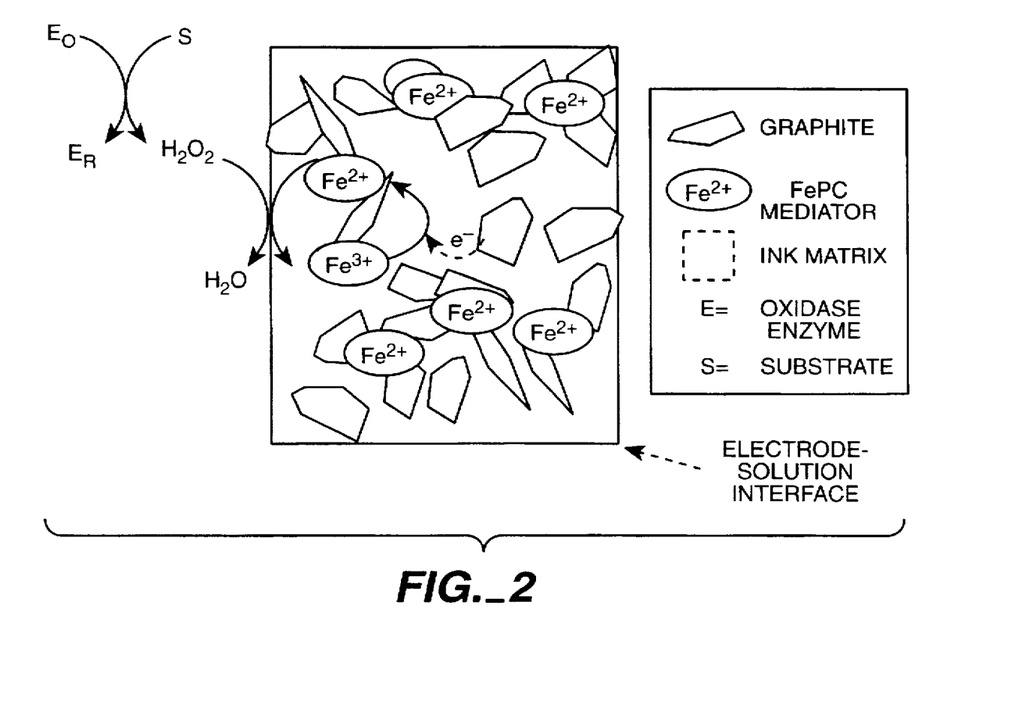
FIG. 2 illustrates an electrode material, such as graphite fibers or particles, dispersed with a ferro isoindole ringed compound and the sequence of electron transfer events in a proposed catalytic reaction for the reduction of hydrogen peroxide exploiting the electro-reduction of a ferro isoindole ringed compound.

Catalytic carbon-based, electro-catalytic electrodes enable the selective determination of hydrogen peroxide. Other suitable electrode substrates (e.g., platinum, gold, and silver) can be used as well. The present hydrogen peroxide measurement system is based on the classical Fenton-Haber process whereby peroxide chemically oxidizes Fe$^{2+}$ ions (or other metals). The resulting trivalent species is electrochemically reduced by an appropriate potential thus closing the catalytic cycle. One such lay-out is shown in FIG. 1 and FIG. 2, where the electro-catalyst and necessary electrode components are immobilized within a carbon-based matrix. This new catalytic reaction can be harnessed in two- and three-electrode formats. The former can be afforded by printing a pseudo-reference electrode (typically composed of Ag/AgCl in proportions ranging from 10–90%) in close proximity to the working catalytic electrode. This can be used to create a completely disposable assay assembly, which is an especially desirable feature for biomedical analysis where conformation to aseptic practice is crucial.

The biological components (i.e., enzymes) can be printed together or on top of this chemical sensing platform to render each electrode unique and specific to a particular task. Such assemblies can be used for single- or multi-parameter measurement profiles. Other transition metal-based catalysts and modified catalysts can be used which are suitable for disparate applications, for example analyzing organic-phase samples (e.g., oils, paints). Electrode assemblies can be operated in reductive or oxidative modes depending on the complexity of the matrix under examination. For instance, simple media may be interrogated using peroxide anodes (e.g., oxidative transduction), on the other hand, more 'exotic' samples (such as blood and urine) would be analyzed using peroxide-selective cathodes (e.g., cathodic transduction (reduction)).

ELECTRODE ASSEMBLIES

The electrode assemblies of the invention can be configured with a macrocyclic compound in a variety of ways to facilitate 1) electrical contact between an electrode's electrode material and the metallo macrocyclic compound and 2) electrical contact between the metallo macrocyclic compound and a redox enzyme, such as an oxidase, if so desired. As described herein different electrodes and electrode assemblies can be achieved by 1) dispersing an metallo macrocyclic compounds in electrode material, 2) applying an metallo macrocyclic compound to the surface of the electrode, 3) applying a layer over the electrode comprising a metallo macrocyclic compound or 4) a combination thereof. Such electrodes can be configured to measure a wide variety of analytes by providing a redox enzyme that senses the presence of an analyte in a sample, either directly (such as when the analyte is the redox enzyme's substrate) or indirectly (such as with an analyte binding moiety). Such assemblies also permit low voltage measurements of analytes which reduces noise, increases selectivity and increases the signal to noise ratio.

ELECTRODES

One embodiment of the invention is an electrode assembly comprising 1) a first hydrogen peroxide electrode comprising a metallo isoindole ringed compound dispersed in an electrode material, and 2) an first enzyme layer comprising a first enzyme and in electrical contact with said first hydrogen peroxide electrode. Such an electrode provides for excellent hydrogen peroxide selectivity, especially for the detection of hydrogen peroxide at low voltages. The catalytic oxidation of hydrogen peroxide can be detected at more positive voltages as well. The electrode preferably has a large surface area and a surface structure that the permits close association of a metallo isoindole ringed compound with a first enzyme in a first enzyme layer. Such close proximity facilitates electro-chemical communication, in this case electron transfer between a metallo isoindole ringed compound and a reaction product, such as hydrogen peroxide. Preferably, the metallo isoindole ringed compound coordinates Fe, Ru, Rh, or Mn.

A variety of electrode materials may be used in such electrodes, particularly materials that present a large surface area to a metallo isoindole ringed compound. Preferably, an electrode, especially an hydrogen peroxide selective electrode, will use electrode materials such as platinum, gold, silver and carbon. Such electrodes, particularly carbon or gold electrodes, can optionally comprise a second metallo macrocyclic compound, such as metallo isoindole ringed compound.

Preferably, electrodes, especially hydrogen peroxide electrodes (which could be used in disposable assay kits), are made of electrically conductive carbon. In both the preferred and non-preferred embodiments the amount or concentration of the metallo isoindole ringed compound provides for sufficient electron transfer to permit detection of an electrical current. Usually, the electrical current measured from either preferred or non-preferred embodiments of the invention in the presence of a metallo macrocyclic compound (such as a metallo isoindole ringed compound) will be greater, less noisy and less prone to interfergents, or more reproducible than in the absence of the metallo macrocyclic compound. For carbon based electrodes, preferably the metallo isoindole ringed compound is $C_{32}H_{18}N_8M$, where M is Fe or Mn. Such metallo isoindole ringed compounds are compatible with first enzymes that are redox enzymes. A particularly compatible combination in an electrode is a metallo isoindole ringed compound with the formula $C_{32}H_{18}N_8Fe(II)$ with a redox enzyme that is an oxidase, particularly an oxidase that catalyses hydrogen peroxide production.

In many applications it will desirable to measure more than one analyte. For instance, a hydrogen peroxide electrode assembly can comprise a plurality of working electrodes configured either as a two or three reference electrode system. Such assemblies comprise at least one additional working electrode (in addition to the first electrode) comprising a second electrode which comprises a metallo isoindole ringed compound usually dispersed in an electrode material, and a second enzyme layer comprising a second enzyme in electrical contact with the second detection electrode. Each additional electrode is usually configured to separately measure the production of a product (e.g. hydrogen peroxide) in response to an additional analyte and is electrically isolated from the other electrodes so as to minimize contamination of other electrical currents and to minimize possible analyte assay reagent contamination.

One way the specificity of an electrode or an array of electrodes used in a multi-analyte detection system can be accomplished is through the use of analyte binding moieties. Analyte binding moieties are chemical structures that recognize a molecular surface or structure of an analyte, and sometimes, when so desired, an analyte analog. Examples of analyte binding moieties include, but are limited to polynucleotides, single stranded oligonucleotides, antibodies, receptors, ligand binding domains, sugar (such as complex carbohydrates), polymers, proteins, non-protein ligands, and recombinant proteins (such as receptors, antibodies and ligand binding domains). For example, in a multi-analyte detection system, such as one that uses hydrogen peroxide electrodes, the first enzyme is attached to a first analyte binding protein that recognizes a first analyte (the analyte is also recognized by a second analyte binding moiety in the vicinity of the first electrode). The second enzyme is attached to a third analyte binding moiety that recognizes a second analyte in the vicinity of a second electrode. The third analyte binding moiety recognizes a different analyte from the first analyte binding moiety. Thus, the third analyte binding moiety permits specific detection of the additional analyte. Such multi-analyte analysis, as well as others, known in the art can be used with the invention described herein.

Analyte binding moieties can also recognize and bind to analyte analogs. Analyte analogs mimic the structure and sometimes the function or partial function of analytes. Analyte analogs include compounds or substances that act as an agonist or antagonist of receptors (or other analyte binding entities) for analytes. Often an analyte analog will have a structure similar to the analyte, except for some chemical modification that confers a different property (or properties) to the analyte analog compared to the analyte.

It should also be appreciated that multi-analyte systems can be used with different electrode embodiments described herein. Preferably, such electrodes will be covered by a enzyme layer and each electrode will have a different enzyme layer, wherein the enzyme may be the same or different from the other enzymes used with the other electrodes and the analyte binding moiety may be the same or different from the analyte binding moieties used with the other electrodes. Preferably, each electrode will have a different analyte binding moiety in electrical contact with the electrode. Preferably, each enzyme layer will comprise a matrix with an analyte binding moiety attached to the matrix. Such multi-analyte detection systems can measure a number of analytes depending on the number of electrodes, such as 4 to 10 or more.

Another embodiment of the invention provides for an electrode, particularly a hydrogen peroxide electrode, that comprises a) a ferro isoindole ringed compound, b) an electrode, and c) an oxidase enzyme. The oxidase has sufficient enzymatic activity to catalyze hydrogen peroxide production in detectable amounts. As described herein any number of oxidases known in the art or developed in the future may used. Preferably, such an electrode comprises electrically conductive carbon used with a ferro isoindole ringed compound, such as $C_{32}H_{18}N_8Fe(II)$ or $C_{32}H_{18}N_8Fe(III)$. The metallo isoindole ringed compound is provided in a sufficient amount to permit electron transfer between the electrode material and the oxidase product, usually hydrogen peroxide, and allow for detection of an electrical current related to catalysis by the oxidase. Usually, the ferro isoindole ringed compound is dispersed in the electrically conductive carbon. Preferably, the ferro isoindole ringed compound mass is at least 1% of the electrically conductive carbon mass. More preferably, the ferro isoindole ringed compound mass is between 3 and 8% of the electrically conductive carbon mass.

Even though the metallo macrocyclic compounds described herein will tremendously improve the selectivity and sensitivity of electrodes, it can be desirable to include an additional selectively reducing interferents means. For instance, a hydrogen peroxide electrode can further comprise a selectively permeable layer either 1) between the oxidase and the hydrogen peroxide electrode or 2) covering both the oxidase and the hydrogen peroxide electrode. Thus, the selectively permeable layer can exclude small (100–800 mw), medium (700–2500 mw) or (greater than 2250 mw) large molecular weight interferents from said hydrogen peroxide electrode. If the selectively permeable membrane is between the oxidase and the electrode, it is preferably permeable to the oxidase's reaction product, while retarding the passage of its substrate. If the selectively permeable membrane covers both the oxidase and the electrode, it is preferably permeable to the oxidase's substrate, by not large molecular weight components of the sample.

When used in conjunction with an redox enzyme, such as an oxidase, the ferro isoindole ringed compound may not be dispersed in the electrically conductive carbon. Instead it can be present in a layer covering the electrode, such as on its surface. Alternatively, electrodes can have a ferro isoindole ringed compound both dispersed in the electrode material and coated on its surface.

Usually, the electrodes of the invention will be covered by a layer comprising a matrix that permits electrical communication with the sample or sample buffer. Electrical communication as used herein refers to the ability of electrically conductive material or fluid to conduct an electrical current. It is understood that electrical communication refers to the ability of the matrix, or other material or liquid to conduct an electrical current when the matrix is wet with a liquid, as well as referring to actual electrical communication in the matrix or other material. In the case of a matrix, electrical communication does not necessarily imply that the matrix is charged, only that the matrix will permit electrical communication. The matrix also usually permits fluid communication between an oxidase and a ferro isoindole ringed compound, so that electro-chemical communication can occur between those two entities. It is understood that fluid communication refers to the ability of a matrix or other structure to fluidly communicate between two points when the matrix or other structure is wet with a liquid, as well actual fluid communication that occurs in the presence of a non-gaseous liquid.

A preferred type of electrode, especially for disposable test cards used in hand-held assay monitors, is a printed electrode. Printed electrodes usually comprise a metallo macrocyclic compound, such as a ferro isoindole ringed compound, dispersed in a printed electrode material. For such electrodes, the printed electrode material either 1) lacks cellulose acetate or 2) has less than 0.25% (mass/mass) cellulose acetate compared to the mass of electrically conductive carbon (or some other electrode material) when the electrode material comprises electrically conductive carbon (or some other electrode material). The electrode material usually comprises electrically conductive carbon printed on an inert solid support, as it is an inexpensive way of producing electrodes and such electrodes are highly selective as described herein. In some cases, to ease the manufacture of the electrode, it will be desirable to disperse an enzyme (such as a redox enzyme or an oxidase) in the electrode material. Preferably, such electrodes are screen printed. Screen printed electrodes usually have a ferro isoindole ringed compound mass that is at least 1% of the electrically conductive carbon mass. For enhanced detection properties the ferro isoindole ringed compound mass can be between 3 and 8% of the electrically conductive carbon mass.

ELECTRODE MATERIALS

A variety of electrode materials may be used in the electrodes of the invention, particularly materials that present a large surface area to a metallo isoindole ringed compound. Preferably an electrode, especially an hydrogen peroxide selective electrode, will use electrode materials such as platinum, gold, silver and carbon. When carbon is used it is usually an electrically conductive carbon and the metallo isoindole ringed compound that provides for sufficient electron transfer to the carbon to permit detection of an electrical current. Carbon in various forms can be used such as fibers, pyrolytic carbon, and rhombohedral crystals. Particle sizes before being printed or applied are usually 0.1 and 50 μ (micron), preferably particles are between 0.1 and 1.0 μ.

ELECTRON TRANSFER COMPOUNDS

The electrodes and methods of the invention can be practiced with a variety of metallo macrocyclic compounds described herein and known in the art. Particularly preferred are the metallo isoindole ringed compounds as they increase electrode selectivity and sensitivity without comprising stability or increasing noise. Such metallo isoindole ringed compounds are particularly good for reducing the voltage required for measurements of redox reaction products, particularly hydrogen peroxide. Metallo macrocyclic compounds are usually selected for their ability to transfer electrons from a product of a redox reaction (catalyzed by a redox enzyme, such as oxidase) to the electrode material. This process can be judged by current voltages relationships in the presence and absence of the product and metallo macrocyclic compound as described herein. Based on this criteria, as well the selectivity experiments described herein, a metallo macrocyclic compound can be selected to use with an electrode to measure a redox product of a redox enzyme catalysized redox reaction. Metallo isoindole ringed compounds include compounds with four isoindole rings (linked in a 16-membered ring) and derivatives thereof. Many of such compounds have the general formula $C_{32}H_{18}N_8M$; where M is Fe, Ru, Rh or Mn and preferably where M is Fe or Mn (the formula and compounds of page 448 of Grant and Hackh's Chemical Dictionary, Editors R. Grant and C. Grant, McGraw-Hill Publishers 1987 is herein incorporated by reference). Ferro isoindole ringed compounds include compounds of the formula $C_{32}H_{18}N_8Fe(II)$ and $C_{32}H_{18}N_8Fe(III)$. The general structural formula for $C_{32}H_{18}N_8M$ is the following:

In addition porphyrins can be used in the present invention. Porphyrins of the following general formula can be used, as well as derivatives thereof:

Porphyrin derivatives known the art such as those of U.S. Pat. No. 4,957,615 issued Sep. 18, 1990 and PCT application WO 93/15174 published Aug. 5, 1993 (the compounds of which are herein incorporated by reference) can be used, especially those containing Fe or Mn.

Derivatives of either metallo isoindole ringed compounds or porphyrins can be used or synthesized (if not in existence) that selectively and catalytically transfer electrons at a desired operating voltage. For example the rings of these compounds can be modified to include substituent groups that provide an electron donating species (or more than one species) (such as —$CH_3$, —$CH_2CH_3$, an alkyl 3–8 carbons in length or —$NH_2$). Such modifications will lower the activation energy to reduce the metal coordinated by the coordinating rings. Thus, the redox potential can be manipulated to facilitate resolution of the oxygen and hydrogen peroxide reduction waves. In the case of hydrogen peroxide, the redox potential for reduction of hydrogen peroxide can be shifted away from the redox potential for oxygen to a more positive potential.

In electrodes with the metallo macrocyclic compound dispersed in the electrode material the amount (mass) of metallo macrocyclic compound used will generally be at least 1% of the mass of the electrode material, which is usually carbon. Usually the mass/mass ratio (metallo macrocyclic compound/electrode material) percent is between 1 to 15%, preferably between 2 to 12% and more preferably between 4 and 9%.

ELECTRODE ASSEMBLY LAYERS

The present invention provides for electrodes that can be optionally covered with an enzyme layer or a selectively permeable layer or a combination thereof. The enzyme layer comprises a first enzyme in electrical contact with an electrode. If the electrode has dispersed within it a metallo macrocyclic compound it will not be necessary to include a macrocyclic compound in the enzyme layer, however it can be advantageous to so if diffusion times into the electrode material appear to be rate limiting. The selectively permeable layer (or layers) can be designed to retard interferents (i.e. compounds that interfere with the detection of electrical signals) or it can be designed to prevent sample components from increasing enzyme activity that is not associated with the presence of an analyte in the sample (i.e. it reduces enzyme activity background).

Normally, the first enzyme layer will comprise a redox enzyme (preferably an oxidase) that catalyses a reaction that results in a product that can be detected by the catalytic transfer of electrons from the product to the electrode material via a metallo macrocyclic compound. The first enzyme layer can also contain additional enzymes that form a series of coupled reactions (including redox reactions) and ultimately result in a product that can be electrically detected. Preferably, the last enzymatically catalysized reaction will result in the production of hydrogen peroxide. If multi-analyte systems with multiple electrodes are used, the first enzyme layer of each electrode can contain a different enzyme to confer specificity for a particular analyte. For example, a first electrode is covered with glucose oxidase, a first enzyme, to directly measure glucose, a second electrode is covered with cholesterol oxidase, a second enzyme, to directly measure cholesterol and a third electrode is covered with lactate oxidase, a third enzyme, to directly measure lactate. Preferably, each electrode and its corresponding enzyme is electrically isolated from the other electrodes.

Preferably, an oxidase can be used in the first enzyme layer that produces hydrogen peroxide. Suitable oxidases include 6-hydroxy-D-nicotine oxidase, alcohol oxidase, aldehyde oxidase, allyl-alcohol oxidase, amine oxidase, bilirubin oxidase, cholesterol oxidase, choline oxidase, cyclohexylamine oxidase, D-amino acid oxidase, D-aspartate oxidase, D-glutamate acid oxidase, dihydroorotate oxidase, dimethyl-glycine oxidase, ethanolamine oxidase, galactose oxidase, glucose oxidase, glycolate oxidase, glycolate oxidase, glyoxylate oxidase, hexose oxidase, L-amino acid oxidase, L-gluconolactone oxidase, L-glutamate acid oxidase, L-ricin α-oxidase, L-sorbose oxidase, lactate oxidase, malate oxidase, N-methylamino acid oxidase, $N^6$-methylrycine oxidase, nitroethane oxidase, nucleoside oxidase, oxalate oxidase, putrecine oxidase, pyranose oxidase, pyridoxine 4-oxidase, pyruvate oxidase, rathosterol oxidase, sarcosine oxidase, sulphite oxidase, tyramine oxidase, urate oxidase, urease and xanthene oxidase.

The oxidase, like any first enzyme, should provide sufficient activity amount of enzyme activity to permit detection of hydrogen peroxide (or other product). Preferably, the enzyme purity is least 80% active enzyme. However, because the detection techniques and electrodes described herein are so sensitive and selective, enzyme preparations with less purity can be used, especially for the manufacture of low cost disposable devices. Typically enzyme activity can range from 100 to 200,000 U/g. The amount of enzyme per electrode will typically vary depending on the activity, temperature, ionic strength, substrate concentration, electrode size, cofactor concentration (if required) and pH. Usually, less than a mg of enzyme will be required per electrode, preferably 10 to 500 μg (micrograms) will be used. Electrodes can also be constructed with 1 to 10 mg per electrode or greater to boost sensitivity. The amount of enzyme used per electrode can also easily be tailored to each specific application and sample type by comparing the current of the electrode as a function of the amount of enzyme per electrode at a constant concentration or amount of substrate.

Alternatively, the use of an enzyme layer may be not desired to facilitate manufacture of the electrode assembly, in which case the enzyme can be incorporated in the electrode material. If enzymes are dispersed in the electrode material, generally the electrode material will not be heated to temperatures that would denature either the lyophilized or dehydrated enzyme. Any of the suitable enzymes mentioned herein and known in the art for redox reactions can be used in such electrodes. Any of the methods or electrode configurations can be suitably combined with such electrodes. Normally, methods that require attachment of the first enzyme to an analyte binding moiety will not be included in electrodes with dispersed enzymes.

Many embodiments of the invention can utilize an enzyme layer with an analyte binding moiety. The enzyme can be attached to a first analyte binding moiety, which is often the case in sandwich assays. Usually, the enzyme is attached to the analyte binding moiety with a covalent bond, however non-covalent bonds can be used (e.g. an avidin labeled enzyme and a biotin labelled antibody). In some situations the first analyte binding moiety will not be bound to a matrix in the enzyme layer and is free to diffuse through the layer, such as in a sandwich assay. Often a second analyte binding moiety will be present in the enzyme layer or in a layer that is in fluid communication with the enzyme layer. In such cases the second analyte binding moiety is usually attached to the matrix either covalently or non-covalently. Both the second and the first analyte binding protein recognize the analyte and can bind the analyte, usually at different positions on the analyte. In some instances, it will be preferable to use multi-sandwich assay in which the first enzyme is indirectly bound to the analyte through multiple binding moieties that bind the analyte in a multi-sandwich manner. Preferably, the first analyte binding moiety is an antibody and is covalently attached to a first enzyme. Redox enzymes, oxidases, and the oxidases specifically mentioned herein can be attached to the first analyte binding moieties for use in assays, particularly sandwich assays. Different types of attachment, either non-covalent or covalent, to the matrix or the analyte binding moiety can also be combined.

If an interferent is a substrate for an enzyme, an enzyme that catalyzes the breakdown of the interferent into an electro-inactive species can be included in the enzyme layer or in another layer in fluid communication with the enzyme layer to reduce the level of the interferent. A scavenger layer comprising a second enzyme can be located between the electrode, particularly a hydrogen peroxide electrode and the first enzyme layer. For example, the second enzyme can be L-ascorbic acid oxidase. The L-ascorbic acid oxidase has sufficient activity to reduce the amount of dissolved oxygen in the presence of its substrate and to reduce the amount of ascorbic acid present in the sample that would normally act as an interferent.

If signal amplification is desired, it can often be accomplished by adding a second enzyme to the enzyme layer that catalyzes the breakdown of a neutral product of the first enzyme into the same product that produces an electrical signal as the first enzyme. For example, the first enzyme is an oxidase which produces a hydrogen peroxide and a substrate for a second enzyme and the second enzyme produces hydrogen peroxide. Such an example is an oxidase that has lactate oxidase activity and produces pyruvate and a second enzyme that has pyruvate oxidase activity.

In another enzyme layer configuration, the enzyme layer comprises a matrix and the enzyme is attached to the matrix, either covalently or non-covalently. Preferably, the first the enzyme is covalently attached the matrix. Redox enzymes, oxidases, and the oxidases specifically mentioned herein can be attached to the matrix for use in assays, particularly assays where the analyte is a substrate for the enzyme. In such assays, preferably the enzyme is directly attached to the matrix, such as in a glucose assay where glucose oxidase is directly attached to the matrix.

The matrix can be made from a variety of matrix materials such as, but not limited to, cellulose, polycarbonate, perfluorinated material, polystrole, polyurethane, polysulphone and silica. Preferably, matrix materials are screen printed onto the electrodes. As described herein a selectively permeable layer between the matrix and the electrode can be desirably and is preferably screen printed.

The enzyme layer can also be comprised of a first enzyme attached to an analyte or analyte analog. Preferably, an oxidase is attached to an analyte or an analyte analog. The enzyme attached to the analyte or analyte analog can prevent the analyte from binding to an analyte binding moiety. Such enzyme layers can be in assays where the analyte is prevented from binding to the analyte binding moiety which is attached to a matrix in the enzyme layer. Enzyme layers with a first enzyme attached to an analyte or analyte analog are particularly useful for competition or displacement assays of the analytes. In such assays, the assay is usually designed to measure a decrease the current in the presence of the analyte compared to the absence of the analyte. The matrix can provide for electrical communication with the electrode, usually a hydrogen peroxide electrode, in the presence of a liquid containing a sufficient amount electrolytes to provide for electrical communication. The matrix in such devices, and other devices described herein, can be part of a fluid guidance pathway that is in fluid communication with a waste reservoir. Usually, the enzyme used in the enzyme layer is provided as a lyophilized enzyme and is dry and covers the electrode.

As described herein, electrodes of the invention can include a layer (or layers) to exclude various assay or sample components. For instance, hydrogen peroxide permeable membranes may be used to isolate the working electrode from potential interferents. A gamut of membrane materials and compositions can be used to eliminate chemical 'cross-talk' (electrochemical and biophysical interferents) by redox-active co-existing compounds encountered in complex samples or assays components (Gilmartin, M. A. T., and Hart, J. P., *Analyst*, 1994, 119, (11), 2431; Lonsdale, H. K., Cross, B. P., Graber, F. M.; Milstead, C. E. In "*Permselective Membranes,*" Rogers, C. E., Ed.; Marcel Dekker: New York, 1971; pp 167–187; Wang, J.; and Lu, Z.; *Anal. Chem.;* 1990, 62, 826–829; Vadgama, P., and Crump, P. W., Analyst, 1992, 117, 1657; Keedy, F. H., and Vadgama, P., *Biosensors & Bioelectronics,* 1991, 6, 491; Sittampalam, G., and Wilson, G. S., *Anal. Chem.,* 1983, 55, 1608; Johnson, J. M., Halsall, H. B., and Heineman, W. R., *Anal. Chem.,* 1982, 54, 1377; and Emr, S. A., and Yacynych, A. M., *Electroanalysis,* 1995, 7, (10), 913; which are herein incorporated by reference). These may be categorized into three distinct groups namely, electro-polymerized, solvent-cast and composite membranes. These membranes are polymeric in nature and may be deposited or laid down over electrodes, creating mesh-type, cross-linked or continuous phase interfaces. Such membranes prevent unwanted species from interacting with the electrode while retaining the electrode's heterogeneous electron transfer characteristics.

Membranes can be deposited using electro-polymerization. This technique permits 'all-chemical' in situ membrane synthesis (Emr, S. A., and Yacynych, A. M., *Electroanalysis,* 1995, 7, (10), 913; Heider, G. H., Sasso, S. V., Huang, K-M., Yacynych, A. M. and Wieck, H. J. *Anal. Chem.,* 1990, 62, 1106; and Sun, Z., and Tachikawa, H., *Anal. Chem.,* 1992, 64, 1112, which are herein incorporated by reference). Therefore, such techniques are applicable to coating complex surfaces that are also in close proximity with one another in order to facilitate electro-chemical and electron transfer. This provides a particularly desirable method for manufacturing miniaturized and multi-analyte electrodes. The membranes are generally 'grown' from the oxidation of monomers (e.g., diaminobenzene and pyrrole) and may be insoluble, conducting or insulating in nature. Oxidation is accomplished by the electrode current. Such modifications can be used in the preparation of electrodes that work in conjunction with enzymes (e.g. redox or oxidase), as the catalyst may be simply entrapped in the deposited membrane. In particular, immobiization of enzymes within conducting polymers formed during the oxidation of the monomer are especially advantageous, facilitating the control of enzyme deposition and its spatial distribution, while maintaining low instrumentation costs.

Solvent casting of layers can be used with the electrodes of the invention and involves the formation of a layer by evaporation of a polymer solution placed on an electrode surface (Tatsuma, T., Okawa, Y., and Watanabe, T., *Anal. Chem.*, 1989, 61, 2352, which is herein incorporated by reference). Casting is usually used with simple, two-dimensional structures. Layers (cast or otherwise) can include matrices with polarity (hydrophobic/hydrophilic), size-exclusion structures (e.g. porous polymer and fibers), and permeable selective layers. For example, cellulose acetate (CA) can be used to select on the basis of size, and polyurethane can be used to select on the basis of polarity, in order to reject interferents. Polyelectrolyte coatings can be used to selectively exclude certain compounds on the basis of charge. For example, perfluorosulphonate ionomers, such as Nafion, are strong acid cation exchanger polymers and therefore, have a tendency to repel anionic species, while allowing the passage of cations (in particular, divalent hydrophobic cations) to the electrode surface. Other examples include polyester-sulfonic acid), zeolites and Eastman AQ-55D polymers (Wang, J., Rayson, G. D., Lu, Z., and Wu, H., *Anal. Chem.*, 1990, 62, 1924; Rolinson, D. R., Nowak, R. J., Welsh, T. A., and Murray, C. G., *Talanta*, 1991, 38, (1), 27; and Koopal, C. G., Feiters, M. C., Nolte, R. J. M., *Bioelectrochem. & Bioenerg.*, 1992, 29, 159, which are herein incorporated by reference). Because the deposition of casted layers introduces further electrode complexity, such casted layers are not preferred for printed electrodes.

Composite selective layers can be created by combining two or more different types of polymers to produce an anti-interference barrier. For example agarose/latex porous membranes offer exclusion to only macromolecular species and thus would be useful as an external interface (Koopal, C. G., Feiters, M. C., Nolte, R. J. M., *Bioelectrochem. & Bioenerg.*, 1992, 29, 159 and Benmakroha, Y., Christie, I., Desai, M., and Vadgama, P., in *Analyst*, 1995, which are herein incorporated by reference). Sulphonated polyether-ether sulphone composites also provide charge separation characteristics. The marriage of uncharged polysulphone backbone and charged pendent sulphonated groups produces a hydrogen peroxide-specific layer.

ELECTRODE MANUFACTURE

The electrodes and electrode assemblies of the invention can be easily manufactured using a variety of techniques. Because the electrodes can be easily massed produced and the same type of electrode (e.g. hydrogen peroxide electrode) can be used for the assay of many different analytes by simply changing the enzyme or analyte binding moiety or both that are in association with the electrode, the present invention provides for a universal platform on which assays can be performed. Mass producible electrodes and electrode assemblies can be used as universal platforms for monitoring biochemical reactions such as, but not limited to, enzymatic, affinity and receptor-oriented arrangements. These disposable strips or test cards may be fabricated using highly cost- and labor-effective techniques based on, but not limited to, a common printing theme encapsulating screen-, air-brush of ink-jet printing techniques. The electrodes are particularly suitable as base transducers for the assembly of single-use electrochemical assays geared for kit format applications akin to over-the-counter tests available from pharmacists. Such kits can include any of the electrodes, enzymes, analyte binding moieties and reagents described herein and known in the art to be suitable for such applications. A typical electrode arrangement is depicted in FIG. 1, however, the dimensions and configuration of the structures can be modified depending on, for instance, the screen type, ink composition and printing apparatus. Thus, strips or test cards could take the form of simple, single monolithic surface through to multi-strip and interdigitated array configurations by exploiting the inherent versatility of screen-printing, for example.

The invention also encompasses electrode designs based on three-dimensional polishable or renewable macro-electrodes, such as solid and paste-type materials. Such modifications can be performed after the electrodes are applied to a solid support. The electrodes can also be printed as peroxide-specific, catalytic micro-electrodes. These are devices bearing at least one dimension in the micrometer range.

Generally, carbon electrodes are made with a metallo macrocyclic compound, such as ferro isoindole ringed compound, using an amount (mass) that is at least 1% of the electrically conductive carbon mass. Usually, in such electrodes the metallo macrocyclic compound mass is between 1 and 15% of the electrically conductive carbon mass, preferably between 2 and 12% and more preferably between 3 and 8%. Preferably such electrodes are screened printed. Other techniques for applying electrode material can be used so long as the particle size of the carbon is made small enough to provide an increased surface area that presents a surface to allow for electron transfer between the metallo macrocyclic compound and the electrode material. Usually the carbon particles are mill rolled or sonicated or both to break the carbon into particles less the 500 μ. Preferably, the carbon particles are less than 50 μ, more preferably less than 10 μ, and most preferably less than 1 μ. Often the electrically conductive carbon is a plurality of bead- or roll- milled particles, or ultra-sonicated particles and such particles can be applied to the solid support using printing techniques. Particles of electrode material, whether or not they are used for printing carbon based electrode, preferably can pass a screen with 1.0 μ holes. More preferably the particles of electrode material can pass through a 0.25 μ screen. The electrode assemblies, especially the said printed electrode will usually have a thickness between 1,000 and 10 μ with respect to the plane of the solid support, and preferably between 200 and 20 μ. Preferably, the electrodes are made with an interdigitated pattern. The electrodes usually comprise a surface area that fits on test card. The electrodes will usually have a working area with a width between 1 mm to 20 mm wide.

Screen printing techniques can also be used to provide the enzyme layer, other layers discussed herein, coatings of enzyme without a matrix, matrices, insulation layers, fluid guidance pathways and any other reagent necessary for the assay. Such techniques can be readily applied to the present invention (U.S. patent application Ser. No. 08/512,358, filed Aug. 8, 1995, which is herein incorporated by reference).

Printing techniques can provide for any desired pattern of fluid guiding pathways. Generally, a defined printed pattern of a fluid guiding pathway refers to a pattern of printed material that will permit directional fluid transport. Furthermore different "inks" or "pastes" can be applied to produce fluid guiding pathways that can include fluid guiding pathway portions having different flow properties. Generally, the term paste relates to materials at a concentration of 10 to 60% (w/v) typically in water or an organic solvent. Preferably pastes are used in the 20 to 40% (w/v) range. Printing compositions usually range from 1 to 25 poise at 25° C., preferably from 4 to 18 poise at 25° C. and more preferably at 6 to 12 poise at 25° C. The term "flow properties" may refer to properties affecting liquid flow along a fluid guiding pathway or to properties affecting the conveyance of solutes by carrier liquids as in chromatography. Materials can be used to change solute/solvent RF values. RF value refers to the ratio of the distance moved by a particular solute to that moved by a solvent front. For example, printed fluid guiding pathways can be manufactured with a printed layer or layers comprised of two or more different materials ("multi-material") providing different rates of fluid transport. Multi-material fluid guiding pathways can be used when it is desirable to modify retention times of reagents in fluid guiding pathways (such as reduction of retention times, as discussed herein for conjugates, or to increase retention times to allow reactions to occur, e.g., antibody-analyte interactions), prevent non-specific binding, improve the assay sensitivity or improve the reproducibility of analyte assays. Such multi-material fluid guiding pathways can be constructed as a heterogeneous printed layer, where a plurality of materials are mixed together and then printed. Multi-material fluid guiding pathways can be also made by printing multiple layers of materials with different flow properties on top of one another. Multi-material fluid guiding pathways are examples of some types of flow accelerators further described herein.

Printed fluid guiding pathways can be provided with regions containing reagent substances, by including reagent substances in the "inks" used to produce them or by a subsequent printing step. A preferred printing technique to use is screen printing. Such regions are usually referred to as reagent zones. Non-immobilized reagents are preferably printed on materials that release the reagents quickly to the fluid flow to allow for rapid hydration of reagents and less reagent retention. Inert materials are especially suitable for this purpose.

Screen printing techniques are also preferably used for printing fluid guiding pathways, conductivity strips, electrodes and their associated conduction tracks, and for printing reagents at specific fluid guiding pathway locations. Air-brushing may also be used to print fluid guiding pathways. Ink jet printing can be used for printing reagents but is not generally suitable for depositing particulate material greater than 20–5 µ.

Such fluid guidance pathways, when so desired, can an improve the control of the flow of liquid and the subsequent timing of reagent delivery in an assay device. Geometrically defined and printed fluid guiding pathways can be used to guide the fluid flow and can be made of disparate chromatographic materials (such as cellulose, silica gel, silica including silica modified to increase the hydrophobicity of the silica, starch, agarose, alginate, carrageenin or polyacrylic polymer gel and mixtures of such materials) to facilitate appropriate retention of individual reagents and to assist and enhance the sequential delivery of the assay components. Different physical, as well as chemical, properties can be used to affect transit times, e.g., densely packed small particles produce longer transit times than loosely packed larger particles of the same material. Regularly shaped particles can be deposited to form a closely packed regular structure which facilitates the passage of proteinaceous material Generally, printed fluid guiding pathways, especially screen printed fluid pathways, comprise thin layers of matrix sufficiently thick so as to provide enough fluid for a detectable signal and to ensure uniformity. Typically, a single printed layer can vary from 5 to 500 µ in thickness and preferably, 5 to 100 µ or 40 to 100 µ in thickness and more preferably 40 to 100 µ in thickness. Fluid guiding pathways can be made of multiple layers or single layers wherein the total layer thickness is usually 50 to 500 µ and preferably, 75 to 300 µ.

For printed electrodes, a variety of electrode assemblies can be used, including two- and three-electrode-based assemblies. Two-electrode assemblies are preferred because of the ease of operation and printing of the electrodes and conduction tracks. Working electrodes can be catalyzed carbon based, such as rhodinized carbon electrodes like MCA 4 (MCA, Cambridge, United Kingdom). Other electrodes based on a combination of carbon and transition metals, preferably platinum, can be used to facilitate low potential oxidation of enzyme product. Such electrodes help reduce background noise associated with measuring assay products, such as hydrogen peroxide, at higher voltages (600–700 mV versus Ag/AgCl reference electrode) required by other types of electrodes, e.g., pure carbon or pure platinum group based electrodes. Generally, it is advantageous to incorporate in a two-electrode system an auxiliary/reference of sufficient size so as not to limit the current required for the potentiostat. For reference electrodes, Ag/AgCl is typically used in the range of 10 to 90% Ag, although for disposable test cards, 10% is preferable. Electrodes are preferably printed so as to maximize detection, for instance by locating the electrode broadside to the fluid transport, as well as creating an interdigitating pattern between the reference and working electrodes.

ANALYTE DETECTION METHODS

The invention affords detecting analytes using a number of different assay formats. Virtually any assay that can use electrochemical detection as a means for detecting an analyte can be adapted for use with the invention's electrodes and electrode assemblies. Generally, the method for electrically detecting the presence of an analyte comprises: 1) measuring an electrical current from a redox electrode comprising an electrode material and a ferro isoindole ringed compound in fluid communication with a redox enzyme, particularly a oxidase. The redox enzyme catalyses a redox reaction that corresponds to the presence of an analyte and produces a product that either 1) directly chemically oxidizes or reduces said ferro isoindole ringed compound or 2) indirectly oxidizes or reduces said ferro isoindole ringed compound. The present invention can also be used without an enzyme for the direct measurement of analytes that decompose under suitable voltages (e.g. direct measurement of hydrogen peroxide).

Methods of detection will often include applying a voltage field between the redox electrode and a reference electrode assembly in either a reduction or oxidation mode. The mode can be selected so as to avoid reduction or oxidation current peaks associated with unwanted species (non-analytes). For example, the applying step can comprise applying a voltage field between the redox electrode and the reference electrode assembly to permit electro-reduction of the ferro isoindole ringed compound from $C_{32}H_{18}N_8Fe(III)$ to $C_{32}H_{18}N_8Fe(II)$. Usually, the method includes comparing the electrical current in the absence of the analyte and in the presence of the analyte. The method can also include quantitating the amount of the analyte in relation to the amount of the electrical current. Standard curves can be established as a reference point and kits can include standards, as well as negative and positive controls to assure the accuracy of the measurements. The preferred voltage field is between −50 and −450 mV, especially when hydrogen peroxide is being measured either directly as an analyte or as a reaction product that is related to the amount of analyze present in the sample. Preferably, the voltage field corresponds to a current peak or steady state current associated with reduction or oxidation of the product of a redox reaction, such as reduction of hydrogen peroxide.

The methods can also include the step of contacting the analyte with a matrix that provides for fluid communication with a redox enzyme, such as an oxidase. For example, the contacting step can comprise 1) contacting the analyte with an analyte attached to an oxidase or an analyte analog attached to the oxidase. The analyte and either 1) the analyte attached to the oxidase or 2) the analyte analog attached to the oxidase are recognized by an analyte binding moiety. Such methods can be applicable to competitive or displacement assays. Such methods can be suitable combined with other methods and devices taught herein and known in the art.

Alternatively, the contacting step can comprise contacting the analyte with an analyte binding moiety attached to a matrix. The method can further include contacting the analyte with a second analyte binding moiety attached to a redox enzyme, such as oxidase. Such methods are applicable to measuring the analyte in a sandwich assay. The analyte can also be measured in a multi-sandwich assay if so desired by including additional reagents such as secondary antibodies, oligonucleotide probes or their equivalent in the assay. Usually the first and second analyte binding moiety will an antibody, although only one of the binding moieties might be an antibody and the other could be a receptor.

The analyte can be any one of number of different chemical entities including a nucleic acid, simple sugar, carbohydrate, protein, recombinant protein, drug, polymer, antigen, antibody, cell, lipid, polynucleotide, oligonucleotide, biologically active molecule endogenously produced in an organism and biologically active molecule exogenously produced outside an organism. Although the analytes might often be proteins, analytes will also often be non-proteins.

Analyte proteins can be virtually any protein from an organism (e.g. a bacteria, fungus or virus) or synthesized in vitro using manual or automated methods. A protein analyte can be from many organisms, including, but not limited to, A, B and C hepatitis virus, *Bacillus anthracis*, Bovine rhinotracheitis, brachematis, *Brucella abortus*, *Campylobacter jejuni*, chlamydia, *Clostridium botulinum*, coronavirus, cytomegalo virus, *Ebola virus*, *Escherichia coli*, group A strep, herpes virus, HIV, human papilloma virus, Lassa fever virus, *Leptospira interrogans*, *Listeria monocytogenes*, *Maedi visna virus*, *Mycobacterium tuberculosis*, *Mycoplasma bovis*, *Neisseria gonorrhoea*, Salmonella, *Staphylococus aurens*, *Stephanuras dentatus*, swine fever virus, *Taxoplasma gondii*, *Treponema pallidum*, *Vibrae epp.*, *Vibrio cholerae*, Yellow fever virus, *Yersinia enterocolitica*, and *Yersinia pestis*. The methods can also be applied to measuring an antibody or other serological marker associated with an organism, such as those organisms described herein. Usually the analyte is antibody that recognizes an protein or sugar moiety of a microorganism.

Analytes may not be proteins such as β-inbibin, 17α-methyltestosterone, 17β-estradiol, 2,4-D, 2,4,5-T, 3-Acetyl deoxynivalenol, acetaminophen, alachlor, aldrin, amikacin, amitriptyline, amphetamine, atrazine, bacillus thuringensis toxin, barbiturates, BAY SIR 8514, benzodiazepines, bilirubin, caffeine, cannabinoids, carbamazepine, carhamazepine, chloramphenicol, chlorosulfuron, cocaine metabolics, cyanzine, cyclosporin, cyclosporine, DDT, deoxynlvalonel, deoxyverrucarol, desipramine, diacetoxyscirpenol, dibenzofurans, dichlorfop-methyl, dieldrin, diethylstilbestrol, difubenzuron, digitoxn, dioxins, disopyramide, endosulfon, estrogen, ethosuximide, flecainide, gentamycin, group A trichothecenes, hCG, hexoestrol, imipramine, iprodione, kanamycin, kepone, lutenizing hormone, lidocaine, malete hydrazide, metalaxyl, methadone, methamphetamine, methaqualone, methotrexate, N-acetylprocainamide, neitilmicin, nortriptyline, opiates, oxfendazole, paraoxon, paraquat, parathion, polychlorinated benzene, pentachlorophenol, phencyclidiine, phenobarbital, phenytoin, primidone, procainamide, progesterone, quinidine, roridin A, rubratoxin B, S-bioallethin, sterigmatocystin, streptomycin, T-2 tetranltetracetate, terhutryn, testosterone, theophyilline, thyroxine, tobramycin, trenbolone, triadimefon, triazine, valproic acid, valproic acid, vancomycin, warfarin, zearalenone and zeronat.

In many embodiments of the invention the analyte will be the substrate for the redox enzyme, as in the case of many of the oxidases described herein. For example, the analyte can be glucose, cholesterol, lactate, oxalate, pyruvate, bilirubin, galactose, sulphite, xanthene, and glutamate. Analytes can also be oxidase substrates for oxidases described herein. The electrode assemblies and methods described herein can provide for a biochemical 'snapshot' of the state of key physiological metabolites including, but not exclusively, glucose, cholesterol, lactate, and urate. These analytes could be measured singly, using a single apposite enzyme, or on a multi-analyte basis using a disposable strip containing a combination of peroxide-producing enzymes. Also such methods can be used for agro-food applications, such as the crisp industry, which need to monitor glucose levels in potatoes as a consequence of their effect on the aesthetics of the product.

The present invention can be used to measure analytes in a variety of samples, such as those samples commonly found in the various fields described herein. For example, in the health care field analytes can be measured, normally without pretreatment, from such fluids as blood, urine, extracellular fluid, lymph, diluted feces, sweat, mucus and saliva. The enzyme layer mentioned herein can contain components from such samples during usage, particularly analytes. The enzyme layer can also contain predetermined amounts of analytes that are expected in a sample to use as control in a kit or as a calibration sample.

The present invention also provides for the detection of pathogenic micro-organisms. This provides for rapid and to provide unequivocal identification of the etiological agents of infectious diseases including, but not limited to, AIDS (IUV, especially types I and II), hepatitis (strains A, B and C), tuberculosis, chlamydia and gonorrhea. The surface antigens of such pathogens can also be detected by assaying antibodies to such pathogens using a surface antigen (or a portion thereof that bind to the antibody) attached to a matrix, applying the sample with the antibody to be detected (analyte) and then applying an anti-antibody attached an enzyme, such as an oxidase, to detect the binding of the antibody that recognizes the pathogen.

The present invention can also be sued to monitor therapeutic drugs as a safety support mechanism to accompany drug delivery programs. A selection of these pharmaceuticals includes theophylline, salicyclic acid, digoxin, gentamycin, netilmicin, tobramycin, vancomycin, and acetaminophen.

Detection of prescribed abused and illicit substances such as barbiturates, benzodiazepines, cannabinoids, cocaine metabolites, opiates, methadone, amphetamine, methamphetamine and anabolic agents (such as 17B-estradiol, oestrogen, testosterone and progesterone) also be accomplished using the present invention.

Chemical and biological pollutants such as pesticides (organophosphorous, organochloro) heavy metals (lead, cadmium, mercury) and compounds such as dioxins, PCBs, atrazine, *Bacillus thuringensis* toxin, DDT can also be detected using the present invention.

Figure 3A:
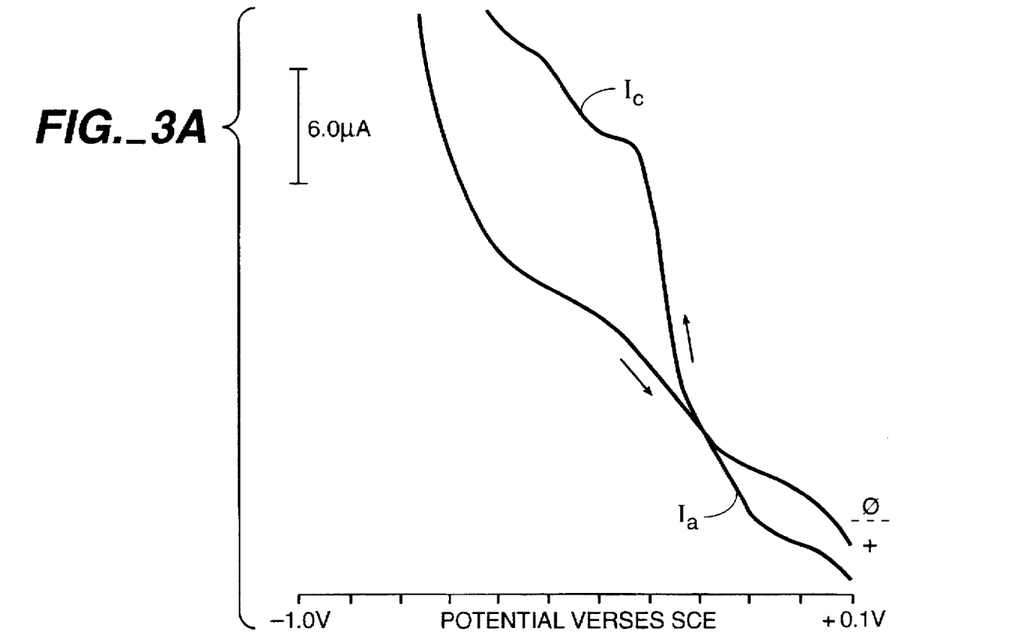
FIG. 3 illustrates DC (direct current) cyclic voltammograms showing the electro-activity of carbon electrodes, such as screen printed carbon electrodes (SPCEs), with a ferro isoindole ringed compound (such as $C_{32}H_{18}N_8Fe(II)$ dispersed in the electrode material. The voltammograms reflect results in anoxygenic solutions. Voltammograms A and B are recorded in plain 0.1 mol dm$^{-3}$ (0.1M) glycine buffer (pH 9) with no hydrogen peroxide and in a similar solution containing $2.2 \times 10^{-3}$ mol dm$^{-3}$ hydrogen peroxide, respectively. The response for an unmodified SPCE is shown in voltammogram C and is recorded in the same glycine buffer using electrodes similar to those electrodes for voltammograms A and B, except that no ferro isoindole ringed compound is present. Electrode areas are 9 mm$^2$ and the scan rate is 20 mV s$^{-1}$. The remaining instrumental parameters: initial and switching potentials, current ranges, scan initiation and direction and galvo zero are shown in the figure.
Figure 3B:
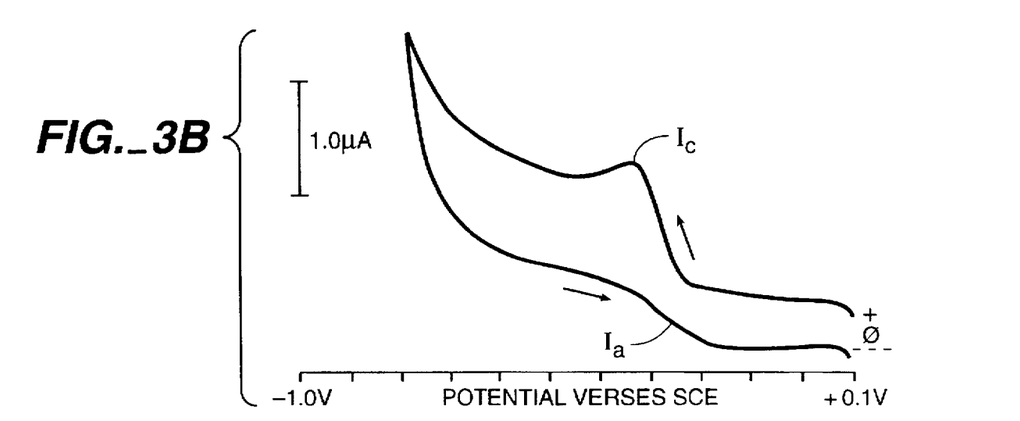
Figure 3C:
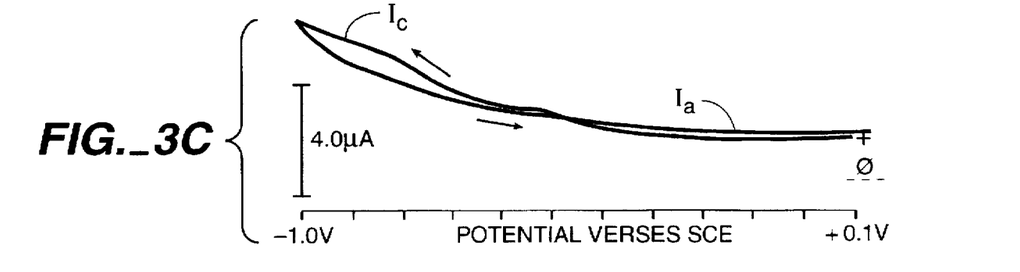

Diagnostic tests for livestock-, food- and water-borne diseases an be made using the present invention. Examples include *Brucella abortus, Escherichia coli* (strain EC10) and *Vibrio cholerae.*

The present invention also allows for the detection of toxins such as *Clostridium botulinum* neurotoxin (A-E), *Staphylococcus aureus* enterotoxin (A-E) and aflatoxins (B1, B2).

The electrodes can also be used without enzymes to detect the non-enzymatic detection of breakdown products in paints and oils.

The invention also includes in vivo electrochemical applications such as, but not restricted to, monitoring brain chemistry, the neuronal propagation and dysfunction, and the detection of damaging free radicals in tissues (e.g. for use in diagnosing arthritis and plant cell damage) with micro-electrodes.

EXAMPLES

CHEMICALS AND REAGENTS

All chemicals are of reagent grade and obtained from BDH, (now Merck, Poole, Dorset, UK) unless stated otherwise. The ink (low resistance carbon based particles), template (stainless steel mesh (100 counts)), apposite solvent system, e.g. (cyclohexanone solution with an alcohol) and facilities for screen-printing are kindly provided by Gwent Electronic Materials (GEM, Pontypool, UK). $C_{32}H_{18}N_8Fe$ (II)As purchased from Kodak (Rochester, N.Y., USA). Ascorbic acid and hydrogen peroxide are obtained from Aldrich (Poole, Dorset, UK). Cysteine, reduced glutathione and uric acid are obtained from Sigma (St. Louis, Mo., USA). Solutions of ascorbic acid, paracetamol, glutathione and cysteine are prepared in 0.05 mol $dm^{-3}$ phosphate prior to use. Uric acid is dissolved in 50 $cm^3$ of 0.05 mol $dm^{-3}$ sodium hydroxide by 20 minutes sonication with a Decon FS100 sonicator (Ultrasonics, Sussex, UK). The supporting electrolyte used throughout is phosphate buffer, which is prepared from stock solutions of 0.5 mol $dm^{-3}$ of sodium dihydrogen-ortho-phosphate and ortho-phosphoric acid. These are mixed to give a buffer of the required pH and diluted with water, de-ionized with an R0200-Stillplus HP system (Purite, Oxfordshire, Thame, UK), to yield the desired concentration. The stability of hydrogen peroxide is followed by titrating against acidified potassium permanganate which is also obtained from Aldrich as a 0. 1N volumetric standard in water.

VOLTAMMETRY AND AMPEROMETRY

Cyclic voltammetry is performed using a Metrohm E612 VA-scanner (Herisau, Switzerland) in conjunction with an E611 VA-detector; these are connected to a Linseis LY18100 x-y plotter (Recorder Laboratory Services, Surrey, UK) to record the voltammograms. A one-compartment cell is employed incorporating an SPCE as a working electrode and platinum and saturated calomel electrodes (SCE) as counter and reference electrodes, respectively. Solutions are ebulliated with nitrogen for anaerobic experiments. Hydrodynamic conditions are achieved using a stirrer and magnetic stirrer bar.

Oxygen and nitrogen are delivered via a system of pipes and the partial pressures of the former gas monitored using a portable oxygen meter (Oxymon, UK). This instrument detected the oxygen concentration amperometrically at −0.7 V vs Ag/ACI.

EXAMPLE 1

ELECTRODE FABRICATION

Working electrodes, which in these examples are used to measure hydrogen peroxide, can be prepared as follows. A 5% (m/m) $C_{32}H_{18}N_8Fe(II)$ loading (5 g of $C_{32}H_{16}N_8Fe(II)$ per 100 g of carbon ink) is mixed with a base carbon ink (code: D14, Gwent Electronic Materials, Pontypol, UK) for 10 minutes by hand using a mortar and pestle and then passed through a roll mill three times with a decreasing gap to make a homogenous ink. Mechanical crushing and milling to a particle size of 10 μ–100 μ (micron) are also acceptable. An inert 1 mm thick, PVC support (ADP, Bristol, UK) is cleaned with ethanol, allowed to dry and cut to size (approximately 50×50 mm) with a guillotine. The homogeneous ink is then deposited onto the printing template (1 cm before electrode heads) and forced through a stainless steel mesh (100 counts per inch) in one pass to produce the desired electrode pattern on the underlying PVC backing material. A semi-automatic printer (Dek, Dorset, UK) can be used in conjunction with a stainless steel screen (100 counts per inch).

Unmodified electrodes are manufactured in a similar manner except that the ferro isonidole ringed compound is omitted at the ink mixing stage. Usually, no firing processes are used to fix the electrodes to the support. Test strips are wrapped in tissue (to mimmize surface contamination) and left to dry in a cabinet possessing suitable air-flow properties. Once dry, all electrodes are individually cut to size from the solid support. Usually, a conductive strip is trimmed to 15 mm and the working area (9 $mm^2$) of the electrode isolated by a thin strip of insulating tape (RS Components). FIG. 1 shows an example of a electrode assembly that can be used to measure up to five different analytes. The electrodes are then inserted into spade connectors which in turn are connected to the potentiostat via coaxial cables.

EXAMPLE 2

DETECTION OF HYDROGEN PEROXIDE REDUCTION USING VOLTAMMETRIC AND AMPEROMETRIC TECHNIQUES

The current reduction peak for hydrogen peroxide can be measured using cyclic voltammograms. Cyclic voltammograms are initially recorded in plain solutions of 0.1 mol $dm^{-3}$ glycine buffer (pH 9.0) with unmodified and $C_{32}H_{18}N_8Fe(II)$ SPCEs (screen printed carbon electrodes). The electrodes are then used to measure reduction of hydrogen peroxide in the same solution containing various concentrations of hydrogen peroxide. The voltammetric conditions are as follows: initial potential, −0.8 V; scan rate, 20 mV s−1 and switching potential, +1.0 V. All experiments are performed in triplicate (unless stated otherwise), using a fresh printed strip for each run; results represent the mean values for each parameter studied. All results are quoted with reference to SCE, where positive current represents the reduction of hydrogen peroxide.

FIG. 3 shows cyclic voltammograms can be recorded using unmodified and $C_{32}H_{18}N_8Fe(II)$ SPCEs in 0.1 mol $dm^{-3}$ glycine buffer (pH 9) and in the presence of $2.2\times10^{-3}$ mol $dm^3$ hydrogen peroxide (without stirring). The redox processes, denoted $I_a$ and $I_c$, correspond to the respective oxidation and reduction of $Fe^{2+}$ (FeII) and $Fe^{3+}$ (FeIII) ions, respectively, for modified electrodes. The redox potential of the macrocyclic bound $Fe^{2+}/Fe^{3+}$ of the $C_{32}H_{18}N_8Fe$ retained in the complex printing ink matrix is −250 mV (SCE) in glycine buffer. The overvoltage associated with the reduction of hydrogen peroxide is dramatically shifted more anodic (ca 0.5 V) with $C_{32}H_{18}N_8Fe(II)$ SPCEs (3A) when compared to the direct electrochemical reduction of hydrogen peroxide at unmodified SPCEs (3C). This indicates that a catalytic process is present, as no appreciable Faradaic activity is seen with non-metallised $C_{32}H_{16}N_8$ only strips (not shown). The increase in current that occurs at the foot of the $Fe^{2+}/Fe^{3+}$ peak observed in plain solutions (3B), Indicates the active species and is consistent with the presence of divalent metal ion transferring electrons to hydrogen peroxide in hydrogen peroxide containing solutions (3A). The benefits of such catalysis are apparent when the electrodes are evaluated using amperometric transduction. The greatly reduced operating potential produces an unexpected improvement in the selectivity of the electrodes and electrode assemblies, especially at voltages less than −300 mV. Such working electrodes demonstrate a superior selectivity towards hydrogen peroxide, especially the reduction of hydrogen peroxide at negative potentials (such as −350 mV to −50 mV).

EXAMPLE 3

HYDRODYNAMIC VOLTAMMETRY

Hydrodynamic voltammetry can be used to optimize the voltage required to activate the reducton of hydrogen peroxide (with stirring). Hydrodynamic voltammograms are obtained for $2.89 \times 10^{-3}$M hydrogen peroxide solutions. SPCEs are immersed in 0.1 mol $dm^{-3}$, pH 9.0 glycine buffer solutions (20 $cm^3$). The applied potentials of the working electrodes are then increased in 50 mV steps. The resulting steady-state cathodic current responses are plotted versus applied voltage in FIG. 4. Each experiment is performed in triplicate with a fresh electrode and the results represent the mean current values.

Figure 4:
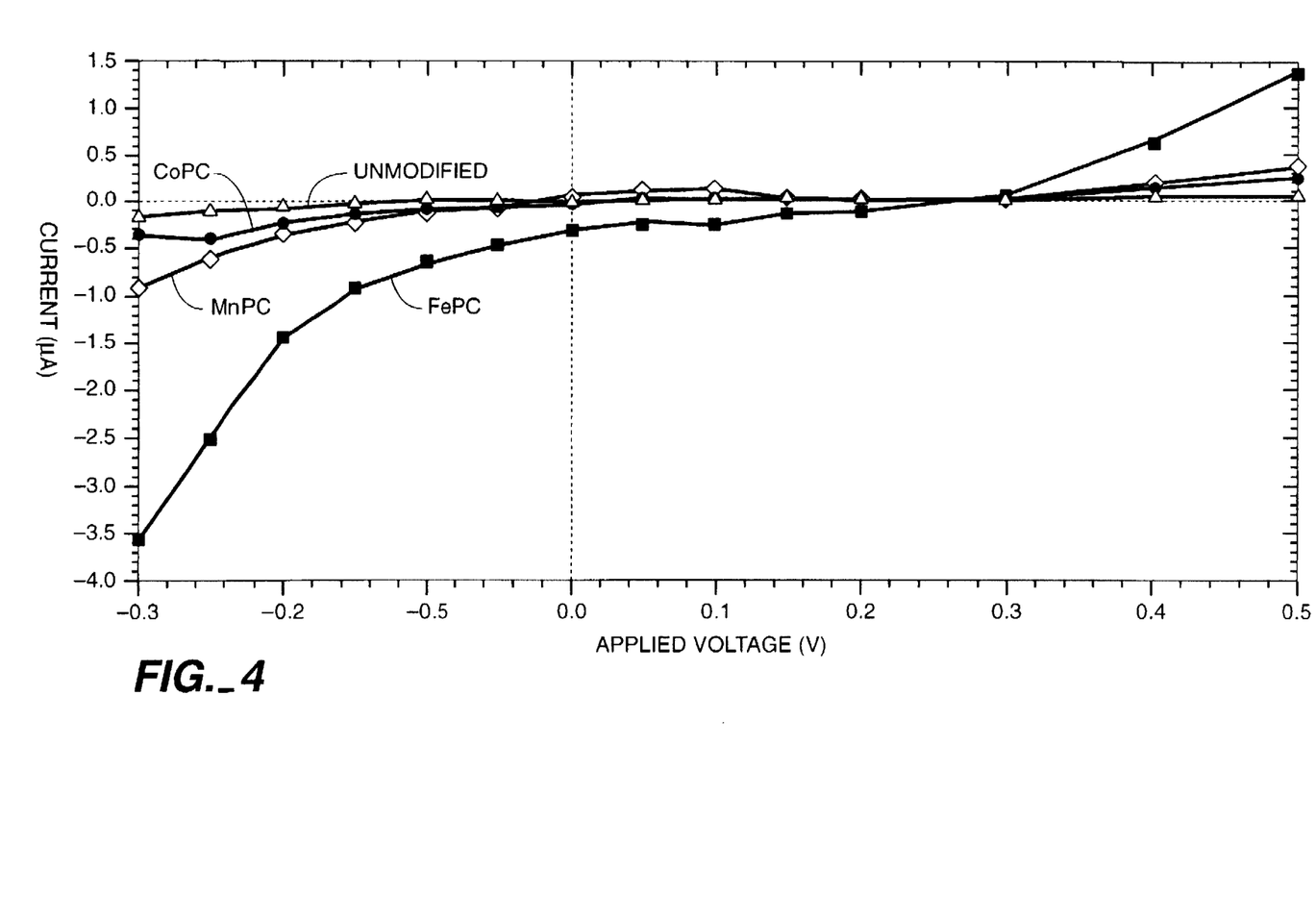
FIG. 4 illustrates hydrodynamic voltammograms (µA (currents) and V (volts)) of $2.2 \times 10^{-3}$ mol dm$^{-3}$ hydrogen peroxide at unmodified, $C_{32}H_{18}N_8Co(II)$, $C_{32}H_{18}N_8Mn(III)$, and $C_{32}H_{18}N_8Fe(II)$ SPCES. The supporting electrolyte is the same as in FIG. 3. The instrumental parameters are the following: time base, 0.5 mm s$^{-1}$, applied voltage; 50 mV increments, and stirring rate; 4 (teflon coated magnetic stirrer).

FIG. 4 shows that raw data can be obtained from hydrodynamic voltammetric experiments using a variety of modified and unmodified electrodes. Clearly, the most efficient vehicle for selective peroxide determination can obtained using $C_{32}H_{18}N_8Fe(II)$ SPCEs, followed by $C_{32}H_{18}N_8Mn(III)$ and $Co(II)$. The current density with Fe(II) is at least two times the current density with Mn(III) and at least four with Co(II). Little activity is obtained with strips lacking an organometallic catalyst, such as a metallo isoindole ringed compound.

EXAMPLE 4

AMPEROMETRIC CALIBRATION AND INTERFERENCE STUDIES

Amperometry at a fixed potential in a stirred solution can be used to evaluate the electrode characteristics of hydrogen peroxide-specific electrode assemblies. A baseline is established in 20 $cm^3$ of 0.1 mol $dm^{-3}$ glycine buffer (pH 9.2). The current will increase in the cathodic response, following (10–100 ml) additions of an $2.9 \times 10^{-3}$M hydrogen peroxide stock solution (approximately 145 µM final concentration). The current can be linearly recorded over a wide range of micromolar to millimolar concentrations.

Figure 5:
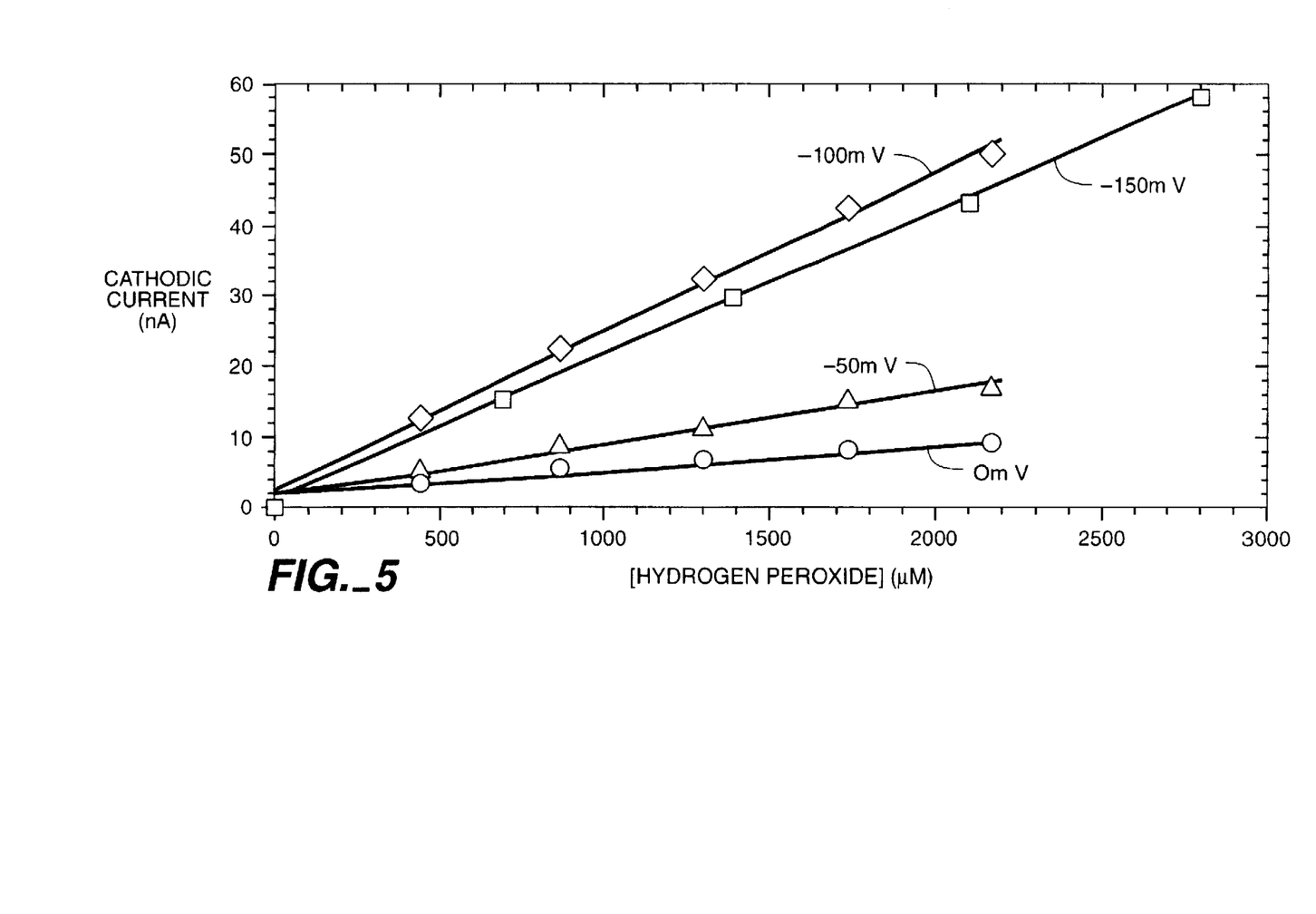
FIG. 5 illustrates amperometric cathodic calibrations of hydrogen peroxide using $C_{32}H_{18}N_8Fe(II)$ SPCES. Instrumental parameters are the same as in FIG. 4 except the potential is fixed according to the graph legend.

FIG. 5 shows a typical amperometric calibration can be obtained for hydrogen peroxide (at hydrogen peroxide reduction voltages), using the $C_{32}H_{18}N_8Fe(II)$ SPCEs described herein. Such results show that $C_{32}H_{18}N_8Fe(II)$ provides a useful analytical signal for measuring the reduction of hydrogen peroxide, which is a product of many oxidase catalyzed reactions. TABLE 1 shows calibration data for the catalytic reduction of hydrogen peroxide using modified screen printed electrodes using different voltages. The experimental conditions are the same as FIG. 5. RSD refers to the relative standard deviation.

TABLE 1

| Eapp (mV) | Response Factor (µA/µmol $dm^3$) | Correlation | RSD (%) | Intercept (nA) |
|---|---|---|---|---|
| 0 | 0.004 | 0.983 | 7.9 | 0.89 |
| −50 | 0.008 | 0.995 | 6.0 | 1.52 |
| −100 | 0.014 | 0.998 | 8.1 | 1.54 |
| −150 | 0.021 | 0.999 | 23.1 | 0.00 |
| −200 | 1.601 | 0.983 | 27.2 | −54.2 |

Amperometry can also be used to test the selectivity of the electrode or electrode assemblies to a number of naturally-occuring or synthetic compounds that may hamper hydrogen peroxide analyses. A baseline is established as described herein using a glycine buffer and several selected interferents can be introduced in the solution in contact with the electrode to yield micromolar or millimolar final concentrations.

Figure 6:
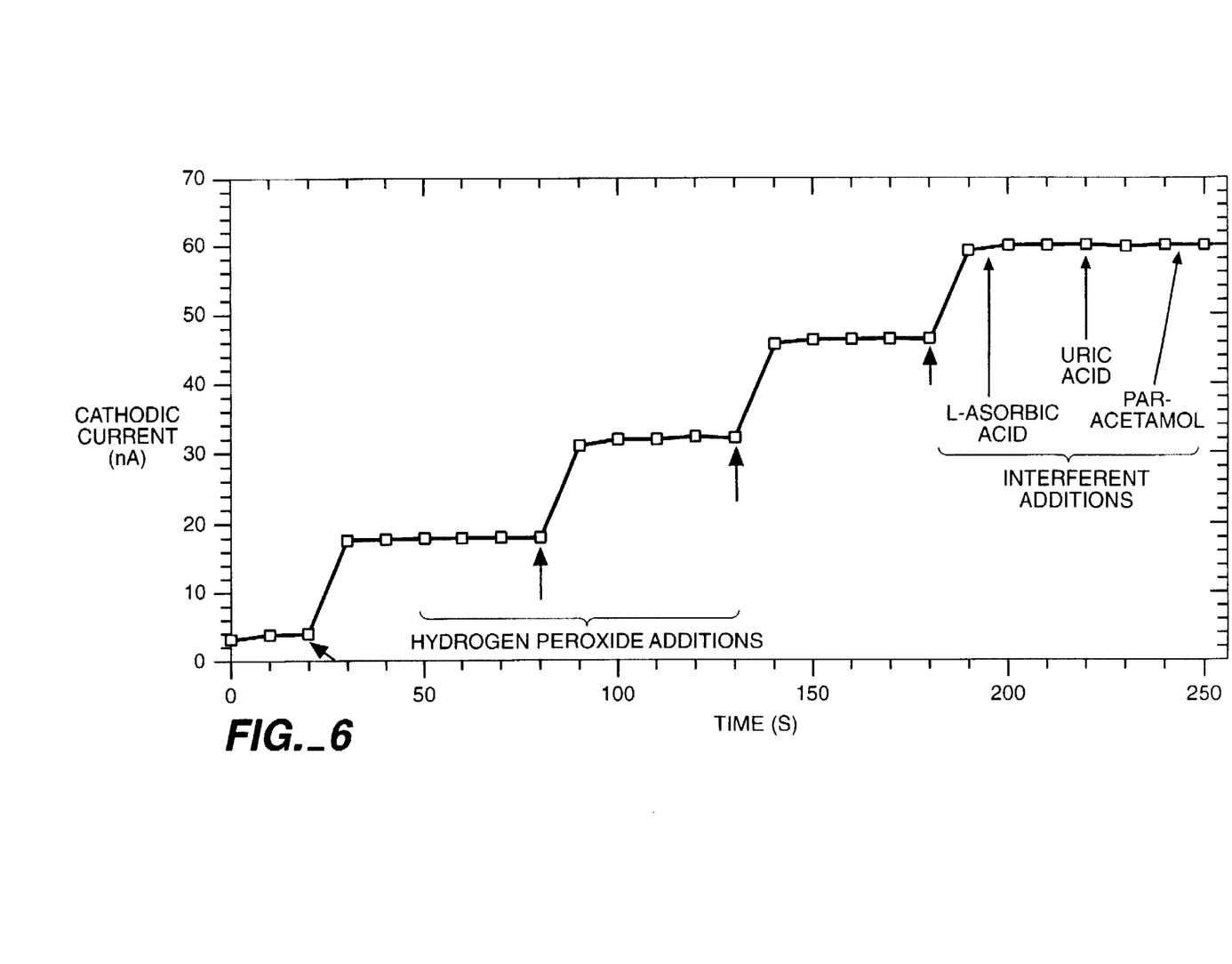

FIG. 6 shows that a representative amperogram can be performed with an $C_{32}H_{18}N_8Fe(II)$ SPCE biased at −0.1 V. Such results show the analytical performance of such electrodes is surprisingly excellent, producing a rapid response time (10s at 95% of the maximum steady-state current), and accurate responses to the analyte over a wide dynamic range (hydrogen peroxide additions were $1 \times 10^{-6} - 30 \times 10^{-3}$ mol $dm^{-3}$), r=0.999, n=3 (slope of hydrogen peroxide concentration and current)). In particular, additions of three notorious interferents, ascorbic acid, uric acid and acetaminophen (paracetamol) at concentrations well above physiological concentrations can show no appreciable current responses. Such experiments can further substantiate the highly selective sensing capabilities of this system. For confirmatory purposes catalase, an enzyme that specifically degrades hydrogen peroxide, can be introduced into the solution. The resulting dramatic diminution in the signal provides conclusive evidence that hydrogen peroxide is the molecule being detected.

The electrodes described herein are surprisingly stable under normal operating and storage conditions, as there is no appreciable loss of catalytic capability during operation or storage. Examination of the efficiency of the electrodes over a four month period, i.e., the mean slopes of three separate calibrations, will show that they retain full reactivity, which is a particularly desirable feature for mass produced electrodes that desirably have a long shelf life. The efficacy of ink mixing and electrode printing for the relative standard deviation of inter- and intra-batch electrode fabrication, can be determined voltammetrically, and is 4.9% and 6.5% (n=12), respectively (slopes of hydrogen peroxide calibrations). Thus, such electrodes will reduce manufacturing variability of electrodes, particularly screen printed electrodes.

PUBLICATIONS

Armstrong, W. A.; and Humphries, W. G.; *Can. J. Chem.*, 1965, 43, 2576–2581.

Armstrong, F. A., and Lannon, A. M., *J. Am. Chem. Soc.*, 1987, 109, 7211.

Aston, W. J., *Biosensors and Bioelectronics*, 1992, 7, 161.

Bartlett, P. N., Whitaker, R. G., Green, M. J. and Frew, J., *J. Chem. Soc. Chem. Commun.*, 1987, 1603.

Batchelor, M. J., Green, M. J., and Sketch, C. L., *Anal. Chim. Acta*, 1989, 221, 289.

Benmakroha, Y., Christie, I., Desai, M., and Vadgama, P., *Analyst*, 1995.

Brabec, V. and Dryhurst, G., *Studia. Biophysica.*, 1978, 67, 23.

Brestovisky, A., Kirowa, Eisner, E., and Osteryoung, J., *Anal. Chem.*, 1983, 55, 2063.

Bulger, H. A., and Johns, H. E., *J. Biol. Chem.*, 1941,140, 427.

Bulin, M. A., *Chem. In Brit.*, 1994, 3, 23.

Cai, X., Ogorevc, B., Tavcar, G., and Wang, J., *Analyst*, 1995, 120, 2579.

Campbell, A. K.; and Simpson, J. J. A.; *Tech. Metab. Res.*, 1979, B213, 10–17.

Cardosi, M. F., and Birch, S. W., *Anal. Chim. Acta*, 1993, 276, 69.

Cave, S., *Fundholding*, Sep. 21, 1994, 14.

Chi, Q., and Dong, S., *Anal. Chim. Acta*, 1993, 278, 17.

Cox, J. A., and Jaworski, R. K., *Anal. Chem.*, 1989, 61, 2176.

Csoregi, E., Jonsson-Pettersson, and Gorton, L., *J. Biotechnol.*, 1993, 30, 315.

Davies, G., in Biosensors, *Fundamentals and Applications*, eds. Turner, A. P. F., Karabe, I., and Wilson, G., Oxford University Press, Milton Keynes, 1990, p. 247.

Dilena, B. A., Peake, M. J., Pardue, H. L., and Skorg, J. W., *Clin. Chem.*, (Winston-Salem, N.C.), 1986, 32, 486.

Dryhurst, G. and Pace, G. F., *J. Electrochem. Soc.*, 1970, 117, 1259.

Emr, S. A., and Yacynych, A. M., *Electroanalysis*, 1995, 7, (10), 913.

Frew, J. A. and Hill, H. A. O., *Anal. Chem.*, 1987, 59, 933A.

Fujihira, M., Muraki, , Aoyagui, S. *Bull. Chem. Soc Jpn*, 1986, 59, 975.

Gilmartin, M. A. T., and Hart, J. P., *Analyst*, 1992, 117, 1299.

Gilmartin, M. A. T., and Hart, J. P., *Analyst*, 1994, 119, (5), 833–840.

Gilmartin, M. A. T., and Hart, J. P., *Analyst*, 1994, 119, (11), 2431.

Gilmartin, M. A. T., and Hart, J. P., *Analyst*, 1994, 119, (11), 2431.

Gilmartin, M. A. T., *Biologist*, 1995, 42, (5), 213.

Gilmartin, M. A. T., Ewen, R., and Hart, J. P., *J. Electroanal. Chem.*, 1995

Golden, T., Li, R., and Wang, J., *Anal. Chem.*, 1988, 60, 1642.

Gorton, L., and Johnsson, G., *J. Mol. Cat*, 1986, 38, 157.

Guilbault, G. G., and Hodapp, P., *Anal. Letts.*, 1968, 1, (12), 789.

Hall, E. A.G H., in *Biosensors*, Open University Press, Milton Keynes, 1990.

Heider, G. H., Sasso, S. V., Huang, K-M., Yacynych, A. M. and Wieck, H. J. *Anal. Chem.*, 1990, 62, 1106.

Heller, *Acc. Chem. Res.*, 1990, 23, 128.

Hilton, S., *Brit. J. Gen. Pract.*, 1990, 40, 32.

Icaza, M-A., Bilitewski, U., *Anal. Chem.*, 1993, 65, (11), 525A.

Ikeda, T., Matsushita, F., and Senda, M., *Biosensors & Bioelectronics*, 1991, 6, 299.

"*Instruction Manual for YSI Model 25 Oxidase Meter and YSI 25 10 Oxidase Probe*";

Yellow Springs Instrument Co., Scientific Division: Yellow Springs, Ohio, 1975.

Johansson, J.; Jönsson-Petterson, G.; Gorton, L.; Marko-Varga, G.; and Csöregi, E.; *J. Biotech.*, 1993, 31, 301–316.

Johnson, 3. M., Halsall, H. B., and Heineman, W. R., *Anal. Chem.*, 1982, 54, 1377.

Jonson, D., and Cardosi, M., *Electroanalysis*, 1995, 70, 69.

Jönsson, G., and Gorton, L., *Anal. Letts*, 1987, 20, (6), 839.

Keedy, F. H., and Vadgama, P., *Biosensors & Bioelectronics*, 1991, 6, 491.

Klassen, N. V.; Marchington, D.; and McGowan, C. E.; *Anal. Chem.* 1994, 66, 2961.

Koopal, C. G., Feiters, M. C., Nolte, R. J. M., *Bioelectrochem. & Bioenerg.*, 1992, 29, 159.

Kulys, J., and Schmid, R. D., *Bioelectrochem. Bioenerg.*, 1990, 24, 305.

Lewis, B., *Clin. Chem.*, 1992, 28, 2093.

Linders, C. R., Vincke, B. J., and Patriarche, G. J., *Anal. Lett.*, 1986, 19, 1831.

Lonsdale, H. K.; Cross, B. P.; Graber, F. M.; Milstead, C. E. In "*Permselective Membranes*"; Rogers, C. E., Ed.; Marcel Dekker: New York, 1971; pp 167–187.

Lorentz, K., and Berndt, W., *Anal Biochem.*, 1967, 18, 58.

Lötzbeyer, T., Schuhmann, W., and Schmidt, H.-L., *J. Electroanal. Chem.*, 1995, 395, 341.

Maidan, R., and Heller, A., *Anal. Chem.*, 1992, 64, 2889.

Marcinkeviciene, J.; and Kulys, J.; *Biosensors & Bioelectronics*, 1993, 8, 209–212.

Nagy, G.; Gerhardt, G. A.; Oke, A. F.; Rice, M. E.; Adams, R. N.; Moore, R. B.; Szentirmay, M. N.; and Martin, C. R.; *J. Electroanal. Chem.*, 1985, 188, 85–94.

Narasaiah, D.; *Biosensors & Bioelectronics*, 1994, 9, 415–422.

Offer, T. R., *Centr. Physiol*, 1894, 8, 801.

Oyama, N., and Anson, F. C., *J. Eletroanal. Chem.*, 1986, 199, 467.

Paddock, R. M., and Bowden, E. F., *J. Electroanal. Chem.*, 1989, 260, 487.

Palleschi, G. and Turner, A. P. F., *Anal. Chim. Acta*, 1990, 243, 459.

Qi, X.; and Baldwin, R. P.; *Electroanalysis*, 1993, 5, 547–554.

Razumas, V., Kazlauskaite, J., Ruzgas, T., and Kulys, J., *Bioelectrochem. Bioenerg.*, 1992, 28, 159.

Razumas, V., Gorton, L., Emneus, J., and Marko-Varga, G., *Anal. Proc.*, 1995.

Rishpon, J.; Shimshon, G.; Campbell, C.; Davey, J.; and Zawodzinski Jr., T. A.; *Electroanalysis*, 1994, 6, 17–21.

Rolinson, D. R., Nowak, R. J., Welsh, T. A., and Murray, C. G., *Talanta*, 1991, 38, (1), 27.

Rüger, P., Bilitewski, U., and Schmid, R. D., *Sensors and Actuators B*, 1991, 4, 267.

Schumb, W. C.; Satterfield, C. N.; and Wentworth, R. L.; *Hydrogen Peroxide*; Reinhold, New York, 1955.

Scott, L. D., and Bowden, E. F., *Anal. Chem.*, 1994, 66, 1217.

Seitz, W. R.; *CRC Crit. Rev. Anal. Chem.*, 1981, 1.

Sequaris, J. M., Valenta, P. and Numberg, H. W., *J. Electroanal. Chem.*, 1981, 122, 263.

Sittampalam, G., and Wilson, G. S., *Anal Chem.*, 1983, 55, 1608.

Sun, Z., and Tachikawa, H., *Anal Chem.*, 1992, 64, 1112.

Taha, Z., and Wang, J., *Electroanalysis*, 1991, 3, 215.

Tatsuma, T., Ariyama, K., and Oyama, N., *Anal. Chem.*, 1995, 67, 283.

Tatsuma, T., Okawa, Y., and Watanabe, T., *Anal Chem.*, 1989, 61, 2352.

Todoriki, S., Ikeda, T., Senda, M., and Wilson, G. S., *Agric. Biol. Chem.*, 1989, 53, (11), 3055.

Updike, S. J., Shults, M. C., and Kosovich, J. K., *Anal. Chem.*, 1975, 47, 1457.

Vadgama, P., and Crump, P. W., *Analyst*, 1992, 117, 1657.

Wang, J., Golden, T., and Tuzhi, P., *Anal. Chem.*, 1987, 59, 740–747.

Wang, J.; and Lu, Z.; *Anal. Chem.*; 1990, 62, 826–829.

Wang, J., Rayson, G. D., Lu, Z., and Wu, H., *Anal. Chem.*, 1990, 62, 1924.

Wang, J., Fang, L., Lopez, D., and Tobias, H., *Anal. Letts*, 1995, 26, 1819.

Wang, J., Liu, J., Chen, L., and Fang, L., in press *Anal. Chem.*, 1995.

Wang, J., Lu, F., Angnes, L., Liu, J., Sakslund, H., Chen, Q., Pedrero, M., Chen, L., and Hammerich, O., *Anal. Chem. Acta*, 1995, 305, 3.

Wang, J., and Wu, H., *J. Electroanal. Chem.*, 1995, 1–2, 287.

Wollenberg, U., Schubert, F., Pfeiffer, D., and Scheller, F. W., *TIBTECH.*, 1993, 11, 255.

All publications and patent applications mentioned in this herein are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. An hydrogen peroxide electrode assembly comprising:
   a) a ferro isoindole ringed compound,
   b) an electrode, and
   c) an oxidase,
   wherein said oxidase is attached to an analyte or an analyte analog and said oxidase can prevent said analyte from binding to an analyte binding moiety; and
   wherein said oxidase has sufficient activity to catalyse hydrogen peroxide production in detectable amounts.

2. A The hydrogen peroxide electrode of claim 1, wherein said electrode comprises electrically conductive carbon and said ferro isoindole ringed compound is $C_{32}H_{18}N_8Fe(II)$ and said $C_{32}H_{18}N_8Fe(II)$ is in an amount to provide for sufficient electron transfer to permit detection of an electrical current related to catalysis by said oxidase.

3. The hydrogen peroxide electrode of claim 2, wherein said ferro isoindole ringed compound is dispersed in said electrically conductive carbon.

4. The hydrogen peroxide electrode of claim 3, wherein said ferro isoindole ringed compound mass is at least 1% of said electrically conductive carbon mass.

5. The hydrogen peroxide electrode of claim 4, wherein said ferro isoindole ringed compound mass is between 3 and 8% of said electrically conductive carbon mass.

6. The hydrogen peroxide electrode of claim 3, further comprising a selectively permeable layer either 1) between said oxidase and said hydrogen peroxide electrode or 2) covering both said oxidase and said hydrogen peroxide electrode, wherein said selectively permeable layer excludes medium interferents of molecular weight 700–2500 from said hydrogen peroxide electrode.

7. The hydrogen peroxide electrode assembly of claim 6, wherein said electrode is screen printed.

8. The hydrogen peroxide electrode assembly of claim 7, wherein said hydrogen peroxide electrode has a thickness between 1,000 and 50 µ.

9. The hydrogen peroxide electrode assembly of claim 8, wherein said analyte binding moiety is attached to a matrix and said matrix electrically communicates with said hydrogen peroxide electrode in the presence of a liquid containing a sufficient amount electrolytes to provide for electrical communication.

10. The hydrogen peroxide electrode assembly of claim 9, wherein said matrix is part of a fluid guidance pathway that is in fluid communication with a waste reservoir.

11. The hydrogen peroxide electrode assembly of claim 8, wherein said ferro isoindole ringed compound is also present in a layer covering said electrode.

12. The hydrogen peroxide electrode of claim 11, wherein said oxidase is dry and covers said electrode.

13. The hydrogen peroxide electrode assembly of claim 12, wherein said ferro isoindole ringed compound is not dispersed in said electrically conductive carbon.

14. The hydrogen peroxide electrode assembly of claim 13, further comprising a matrix, wherein said matrix permits fluid communication between said oxidase and said ferro isoindole ringed compound.

15. The hydrogen peroxide electrode assembly of claim 14, wherein said ferro isoindole ringed compound is present on a surface of said hydrogen peroxide electrode or said ferro isoindole ringed compound is present in said matrix and said matrix permits electrical communication between said ferro isoindole ringed compound and said electrode.

16. The hydrogen peroxide electrode assembly of claims 15, wherein said oxidase is covalently attached to said matrix.

17. The hydrogen peroxide electrode assembly of claim 15, wherein said oxidase is noncovalently attached to said matrix.

18. The hydrogen peroxide electrode assembly of claim 17, wherein said oxidase is attached to said matrix through a first analyte binding moiety.

19. The hydrogen peroxide electrode assembly of claim 17, wherein said oxidase is attached to said matrix through a second analyte binding moiety, wherein said first analyte binding moiety is covalently attached to said matrix.

20. The hydrogen peroxide electrode assembly of claim 18, wherein said oxidase is attached to a second analyte binding moiety and said second analyte binding moiety is attached to said matrix through an analyte that is attached to said matrix through said first analyte binding moiety.

21. The hydrogen peroxide electrode assembly of claim 20, wherein said ferro isoindole ringed compound is a ferrous isoindole ringed compound.

* * * * *